(12) United States Patent
Omiya

(10) Patent No.: US 6,849,048 B2
(45) Date of Patent: Feb. 1, 2005

(54) IMAGE PROCESSING DEVICE AND ULTRASONIC DIAGNOSTIC DEVICE

(75) Inventor: Jun Omiya, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 13 days.

(21) Appl. No.: 10/396,418

(22) Filed: Mar. 26, 2003

(65) Prior Publication Data

US 2003/0187350 A1 Oct. 2, 2003

(30) Foreign Application Priority Data

Mar. 29, 2002 (JP) ........................................ 2002-097079

(51) Int. Cl.[7] ................................................. A61B 8/00
(52) U.S. Cl. ..................................... 600/443; 128/916
(58) Field of Search ............................... 600/407–472; 367/7, 11, 130, 138; 128/916; 73/625, 626; 382/132; 345/427

(56) References Cited

U.S. PATENT DOCUMENTS

| | | | | |
|---|---|---|---|---|
| 5,083,567 A | * | 1/1992 | Uchibori | 600/455 |
| 5,526,442 A | * | 6/1996 | Baba et al. | 382/132 |
| 5,615,680 A | * | 4/1997 | Sano | 600/437 |
| 5,872,571 A | * | 2/1999 | Arling | 345/427 |
| 6,006,126 A | * | 12/1999 | Cosman | 600/426 |
| 6,283,918 B1 | * | 9/2001 | Kanda et al. | 600/441 |

FOREIGN PATENT DOCUMENTS

| | | |
|---|---|---|
| EP | 1 061 474 | 12/2000 |
| WO | 98 40014 | 9/1998 |

* cited by examiner

*Primary Examiner*—Ali Imam
(74) *Attorney, Agent, or Firm*—Wenderoth Lind & Ponack, L.L.P.

(57) ABSTRACT

An image generation unit generates image data of a tomographic image based on an electric signal received from a send/receive unit through a control unit. An ROI setting unit sets an ROI to the generated tomographic image. A characteristic value extraction unit extracts a characteristic value (such as volume of left ventricular of a heart) to the set ROI. A synchronization generation unit generates a synchronization signal based on the extracted characteristic value. A synchronization information addition unit adds information that represents the generated synchronization signal to image data and stores the image data in an image data storage unit. A data reading unit reads out the image data to which the information that represents the synchronization signal is added from the image data storage unit. An image display unit displays a tomographic image of the read-out image data.

28 Claims, 19 Drawing Sheets

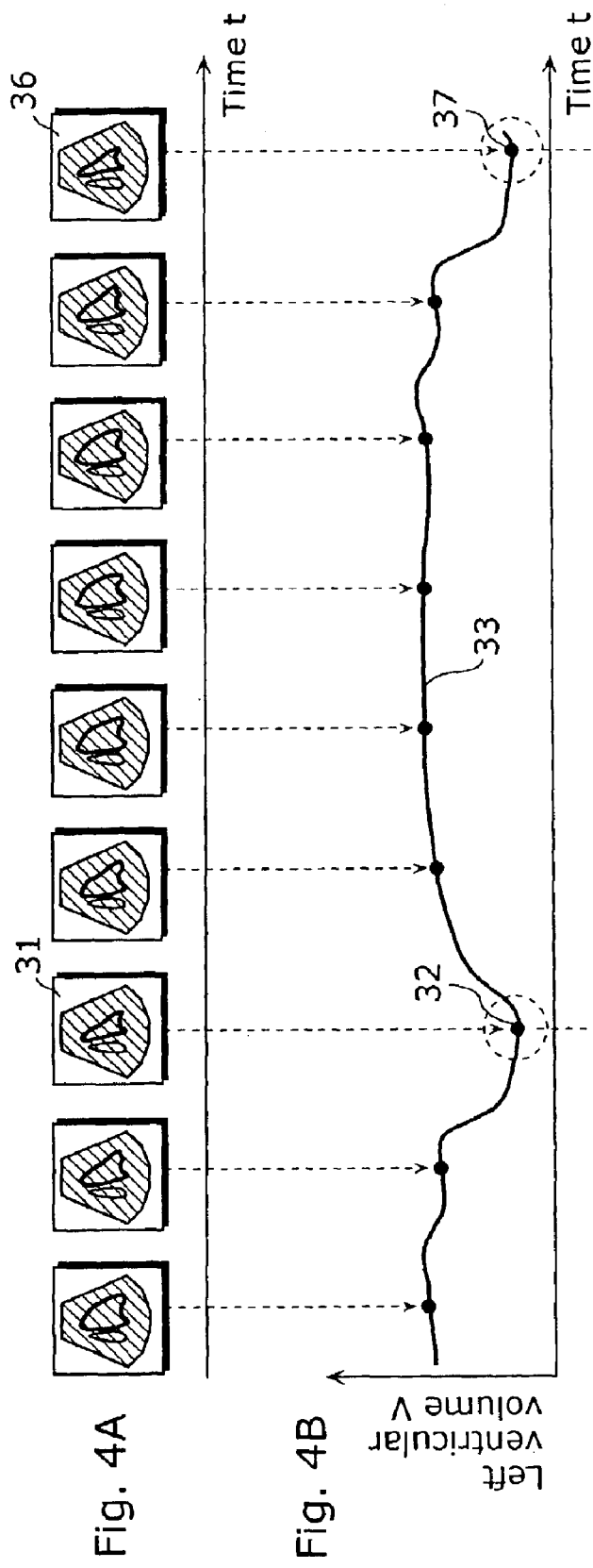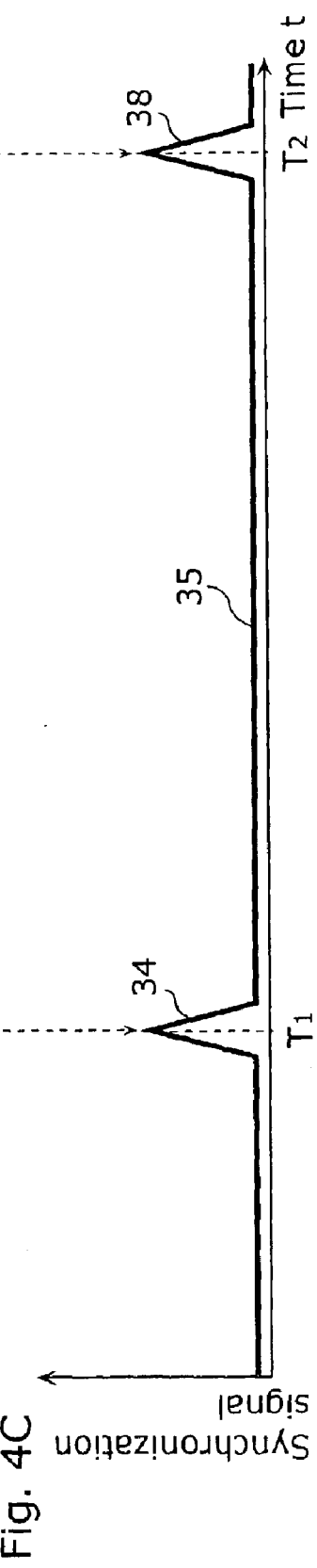

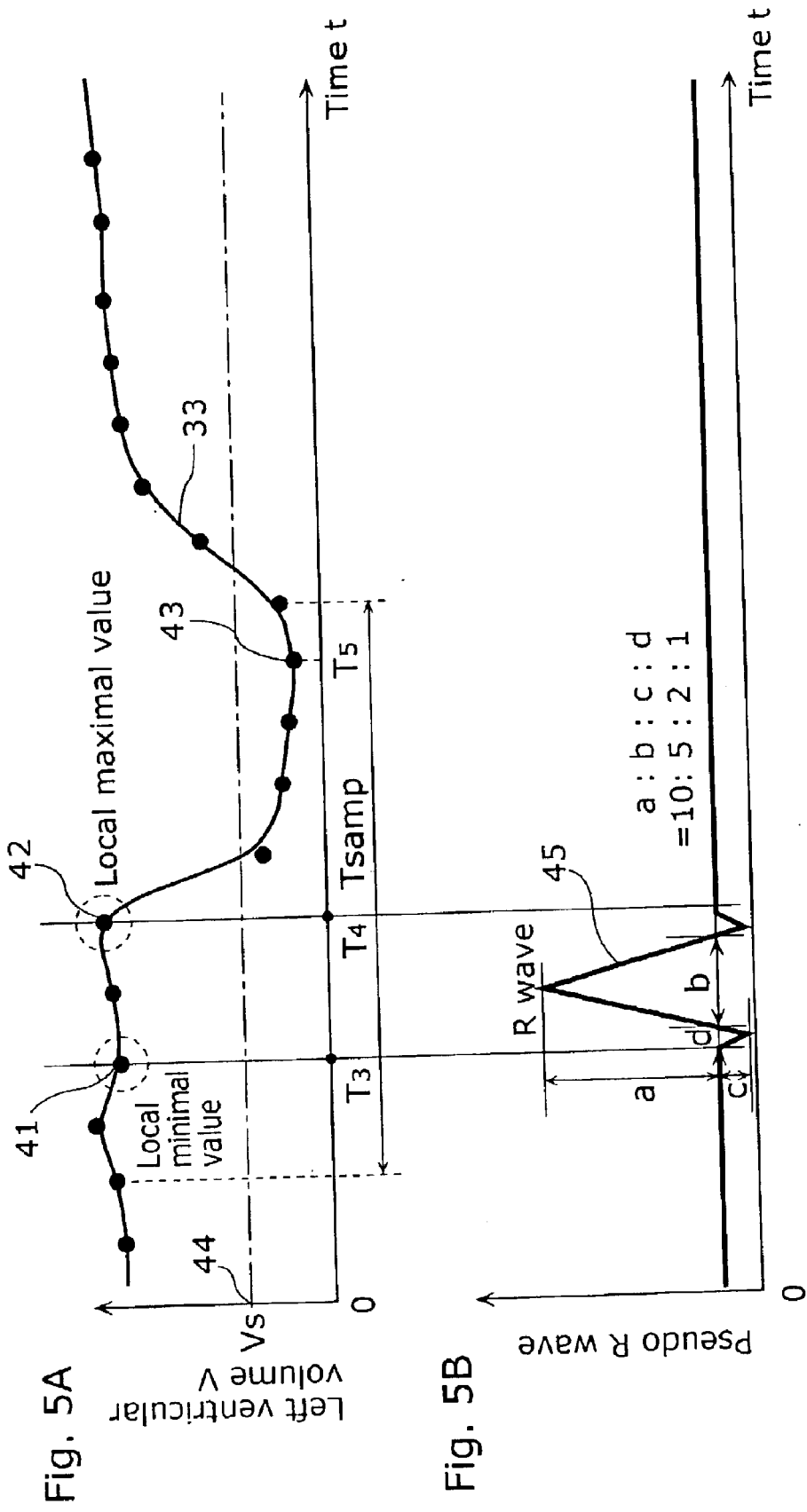

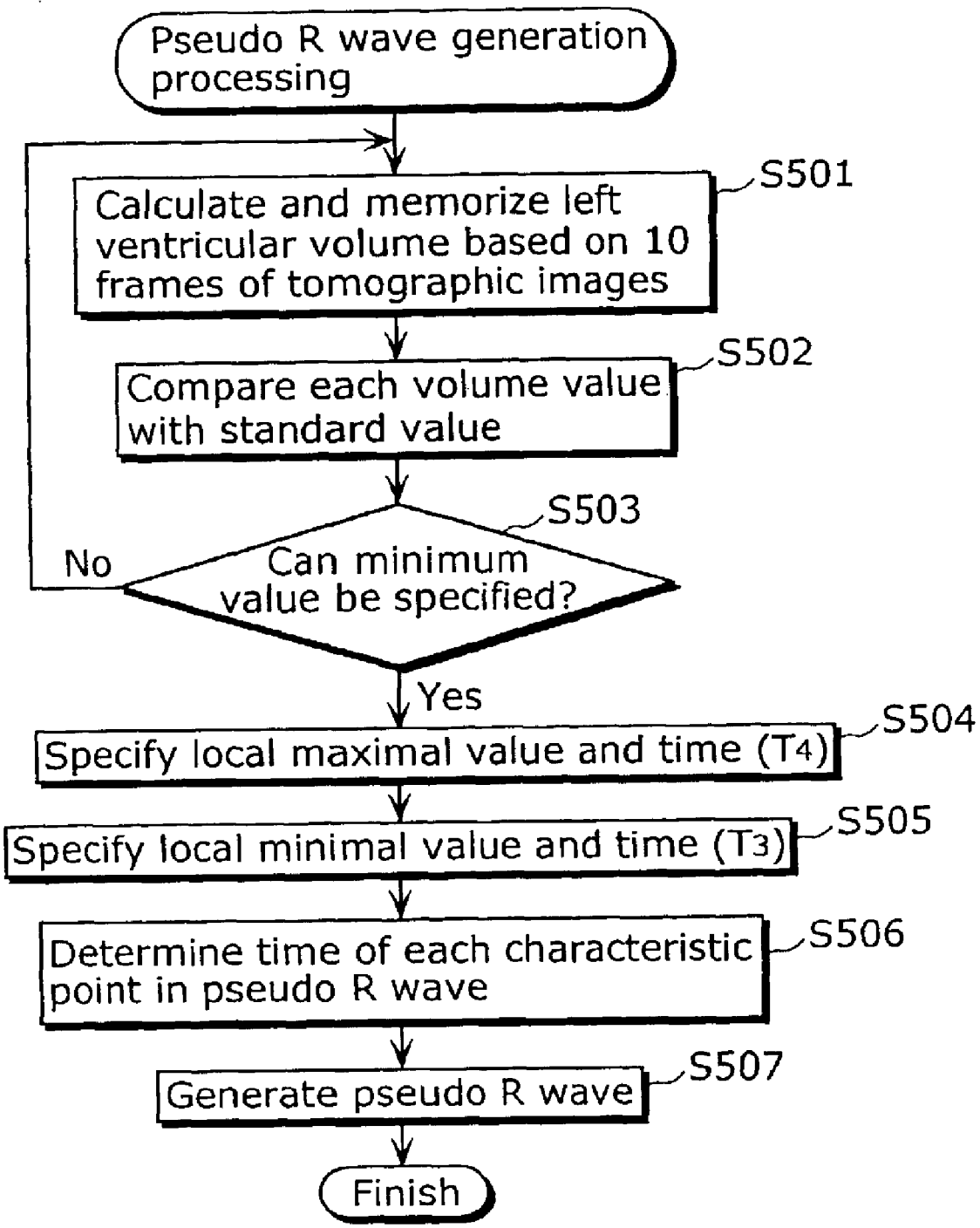

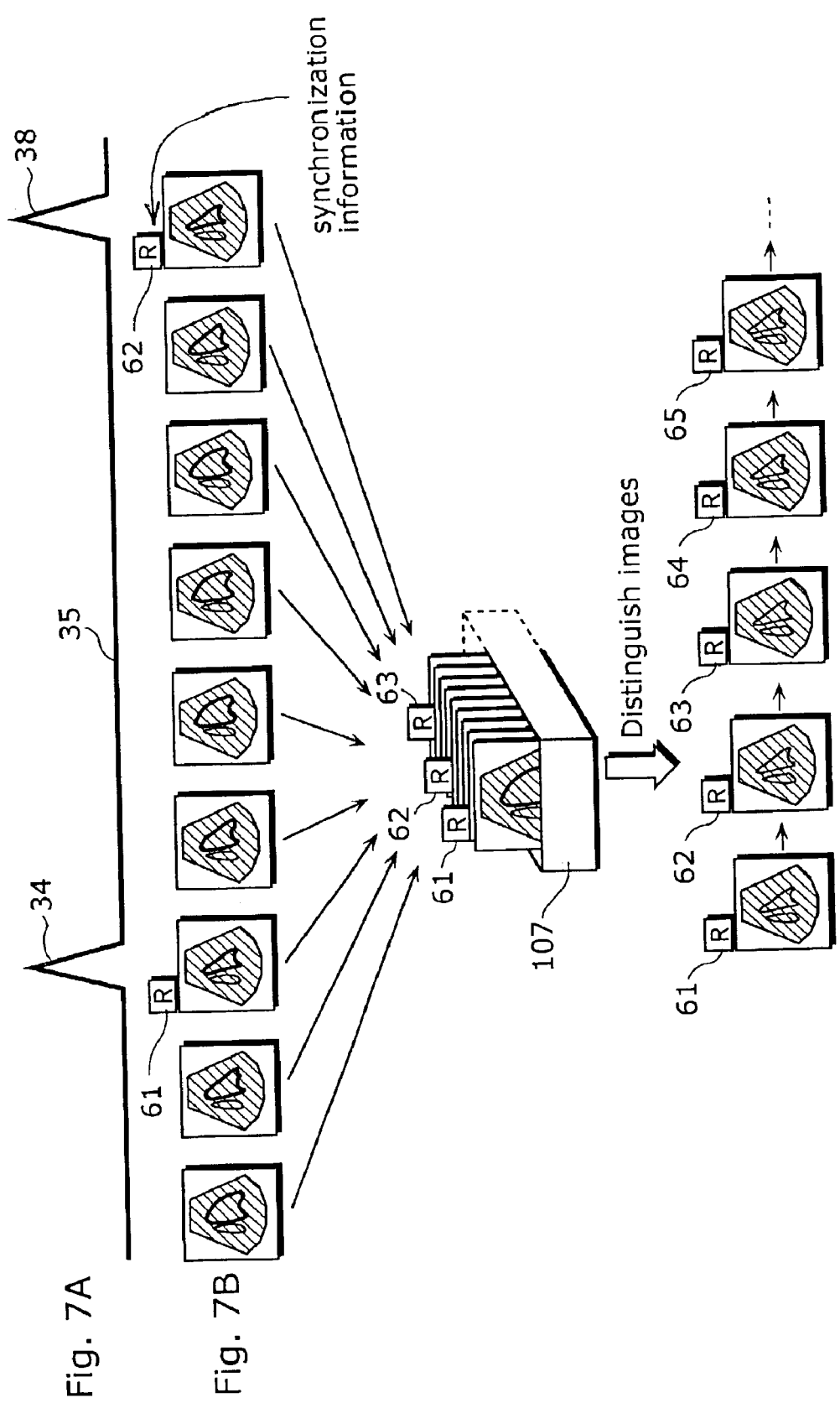

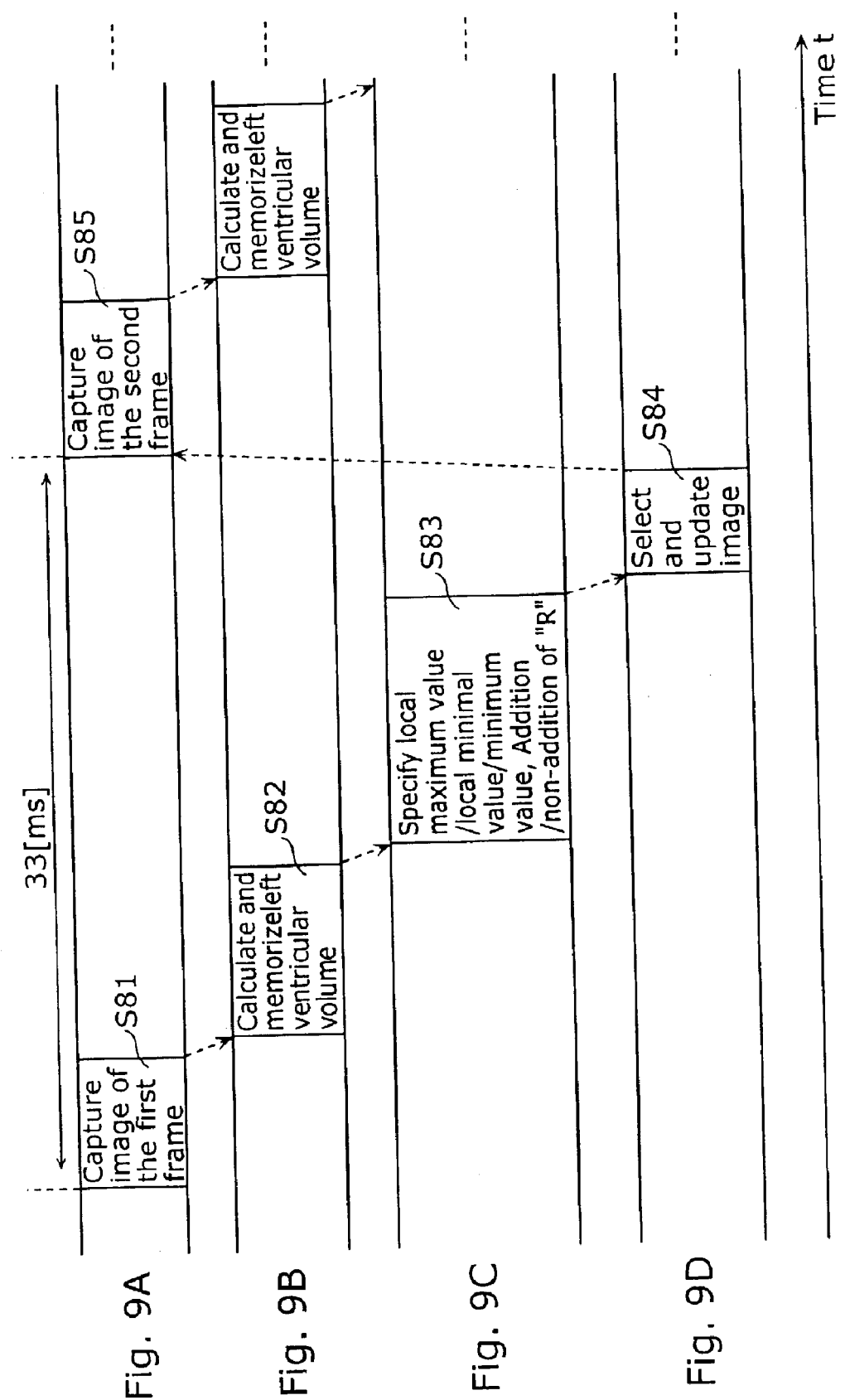

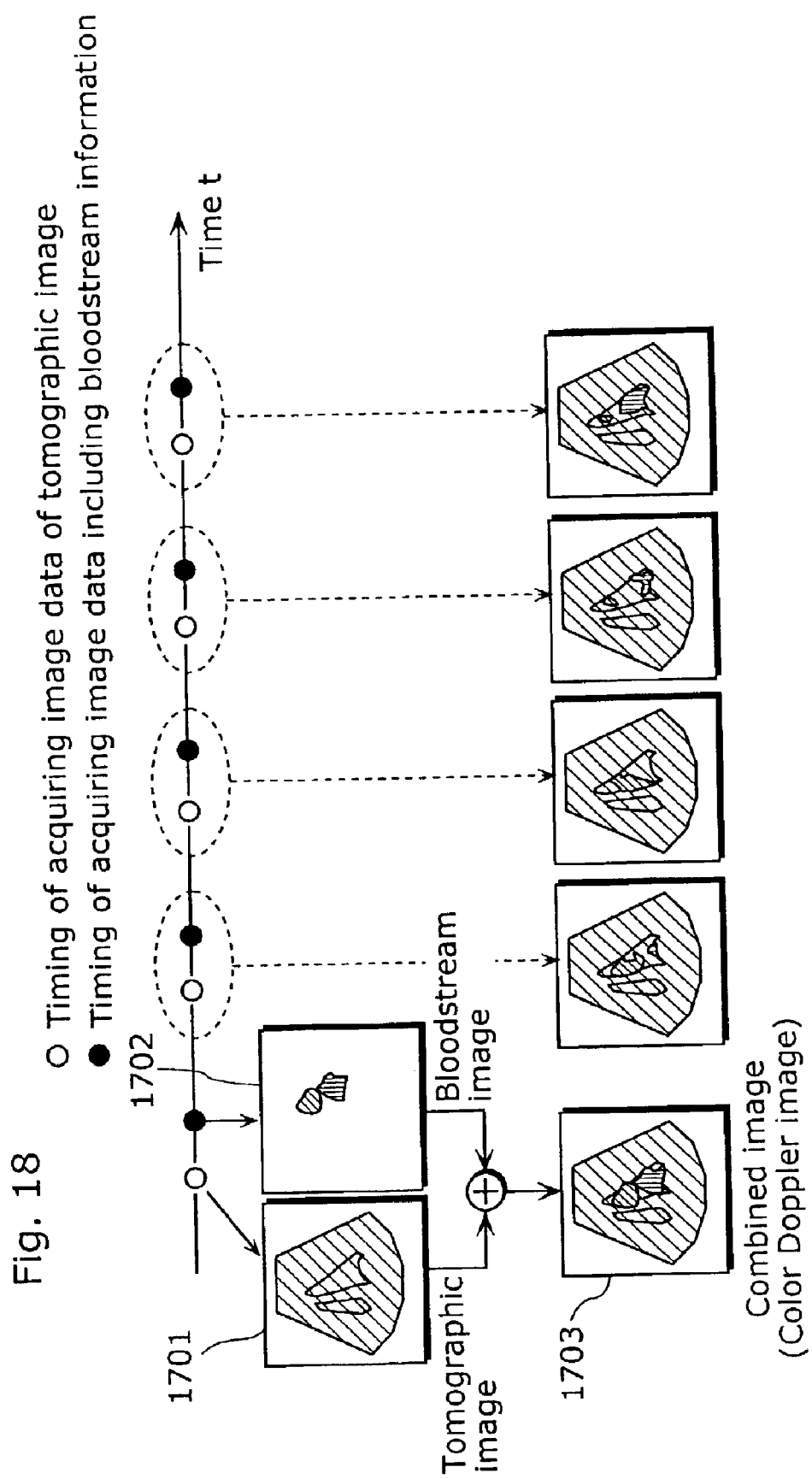

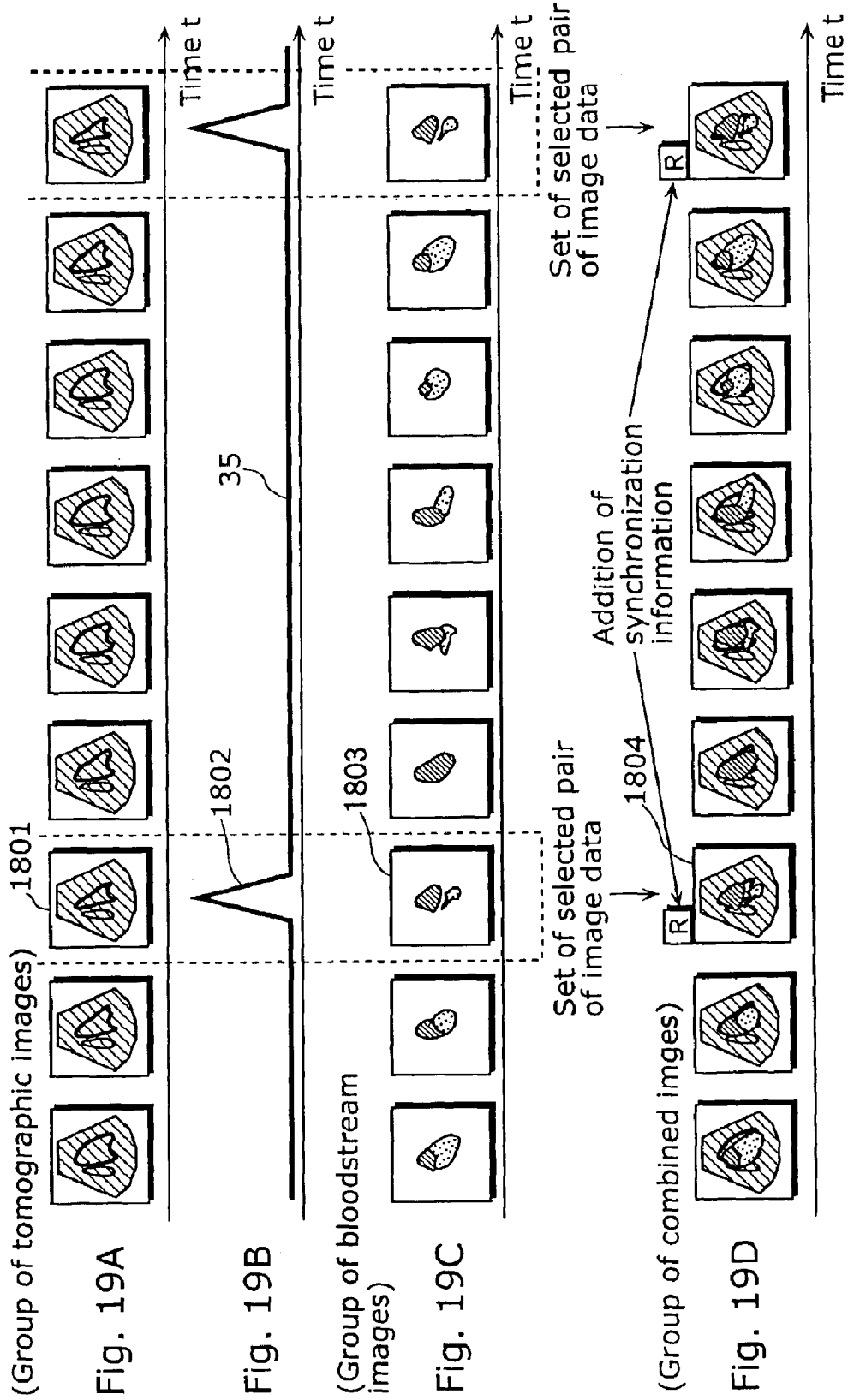

IMAGE PROCESSING DEVICE AND ULTRASONIC DIAGNOSTIC DEVICE

BACKGROUND OF THE INVENTION (1) Field of the Invention

The present invention relates to image display devices such as an ultrasonic diagnostic device and a CT (Computerized Tomography) device, and particularly to an image processing technology for a tomographic image obtained by irradiating an examined object with ultrasound, X rays and the like.

(2) Description of the Prior Art

An image display device irradiates an anatomy (a test subject) with a diagnostic signal. (hereafter called "signal") such as ultrasound and X rays, receives a signal reflected from the anatomy or a signal passing through the anatomy and executes imaging of the inside of the anatomy based on the received signal. In recent years, such an image display device has been widely used in industry and clinical medicine fields. Representative examples of such devices are an ultrasonic diagnostic device using a reflected signal and a CT device using a signal that passes through.

These image display devices can measure the anatomy and execute imaging in real time with the performance of a calculating machine, especially the processing speed, improving. In particular, in the clinical medicine field that needs high time resolution starting from circulatory organs, since a tomographic image of the anatomy is provided in real time, it is possible to quickly diagnose an affected part and the like.

By the way, in a real-time diagnosis, when an operator wants to measure a function, volume and the like of an examined object that operates cyclically, it is necessary to acquire a synchronization signal by some kind of method.

FIG. 1 is an outside view of a conventional ultrasonic diagnostic device 50. As shown in FIG. 1, the ultrasonic diagnostic device 50 is made up of a display device 51, a main unit 52, a probe 53 and an electrode for electrocardiogram (ECG) 54.

The display device 51 is a display device with a liquid crystal, CRT (cathode-ray tube) or the like to display a tomographic image obtained by echography or the like and necessary information. It has a touch panel and the like to accept an input from an operator.

The main unit 52 includes a send/receive circuit that controls transmission/reception of the ultrasound through the probe 53, a signal/image processing circuit made up of a DSP (Digital Signal Processor), RAM (Random Access Memory) and the like and a liquid crystal display that has a group of switches, a mouse and a touch panel to accept the input from the operator. Additionally, the main unit 52 receives an ECG signal through the electrode for ECG 54.

The probe 53 is a search unit made up of an ultrasound vibrator, and an acoustic lens and the like to send/receive the ultrasound.

As just described, the conventional ultrasonic diagnostic device 50 acquires the ECG signal as a synchronization signal from the test object through the electrode for ECG 54.

However, in the case of the conventional ultrasonic diagnostic device, since the above-mentioned synchronization signal is inputted into the ultrasonic diagnostic device through the special-purpose electrode for ECG 54, the ultrasonic diagnostic device needs a special-purpose circuit and a special-purpose cable, and therefore the cost for diagnosis becomes high, and at the same time space to set up an external device is necessary.

In addition, for use in the clinical medicine field, since it is necessary for a patient who is a subject for measurement to wear a measuring instrument to measure or extract the synchronization signal, there is a burden for the patient in both mind and body.

As just described, when making a diagnosis using the synchronization signal, generally the external device is necessary and the subject for measurement also needs to wear the measuring instrument, and therefore, there is a drawback that it is complicated and the measurement cost is high.

SUMMARY OF THE INVENTION

In view of the foregoing, it is the first object of the present invention to provide an image processing device or an ultrasonic diagnostic device that makes an examination using a synchronization signal possible without inputting a synchronization signal from outside. Further, it is the second object of the present invention to provide a display method for making it easy to understand the correspondence between an extracted synchronization signal and a displayed tomographic image.

To achieve the above-mentioned objects, the image processing device according to the present invention is an image processing device that processes a tomographic image of an object that acts cyclically comprising: an image acquisition unit operable to acquire a sequence of image data of a tomographic image by sampling at a constant rate during a predetermined time that is one cycle or more; a characteristic value extraction unit operable to extract in sequence characteristic values that change with a passage of time based on the acquired sequence of image data; and a synchronization signal generation unit operable to generate a synchronization signal that indicates a timing of same phase in the cyclical action based on the extracted characteristic values.

Herewith, since a synchronization signal is generated from the acquired tomographic image (a synchronization signal is obtained without inputting an electrocardiogram (ECG) signal and the like from outside), it becomes possible to execute a diagnosis and a display to an examined object that acts cyclically focusing on a synchronous tomographic image. As a result, since it becomes unnecessary to input a synchronization signal that is conventionally generated by an external device, there is an effect that a simpler diagnosis at a lower cost becomes possible.

Additionally, the image processing device further comprises:

a synchronization information addition unit operable to discriminate a phase timing by which individual image data is sampled in the sequence of image data based on the generated synchronization signal and add synchronization information that indicates phase timings are the same in plural image data.

Herewith, since it is possible to add synchronization information based on the generated synchronization signal and to select only the synchronous data, it becomes possible to display a synchronous tomographic image without inputting a synchronization signal from outside, reducing memory capacity.

Further, the image processing device further comprises: a bloodstream information calculation unit operable to generate bloodstream information that represents physical characteristics of bloodstream based on sampled data by a timing that has a predetermined relationship with sampling timing in the image acquisition unit; a bloodstream image generation unit operable to generate image data of a bloodstream image based on the generated bloodstream information; and a correspondence unit operable to associate image data of the tomographic image to which the synchronization information is added with image data of the bloodstream image based on the synchronization signal.

Herewith, since a synchronization signal is generated form the acquired tomographic image and a color Doppler image such as blood stream is displayed based on this synchronization signal. It becomes possible to associate an ordinary tomographic image with a color Doppler image that have a temporally determined relationship and to display the associated images.

Furthermore, to achieve the above-mentioned objects, the ultrasonic diagnostic device is an ultrasonic diagnostic device that generates and displays a tomographic image of an object that acts cyclically comprising: an image acquisition unit operable to acquire a sequence of image data of a tomographic image by sampling at a constant rate during a predetermined time that is one cycle or more; a characteristic value extraction unit operable to extract in sequence characteristic values that change with a passage of time based on the acquired sequence of image data; a synchronization signal generation unit operable to generate a synchronization signal that indicates a timing of the same phase in the cyclical action based on the extracted characteristic values; a synchronization information addition unit operable to discriminate a phase timing by which individual image data is sampled in the sequence of image data based on the generated synchronization signal and add synchronization information that indicates phase timings are same in plural image data; and a display unit operable to display a tomographic image based on the synchronous image data to which the synchronization information is added.

Herewith, since a synchronization signal is generated from the acquired tomographic image (a synchronization signal is obtained without inputting an ECG signal and the like from outside), it becomes possible to execute a diagnosis and a display to an examined object that acts cyclically focusing on a synchronous tomographic image. As a result, since it becomes unnecessary to input a synchronization signal that is conventionally generated by an external device, an ultrasonic diagnosis device that can execute a simpler diagnosis at a lower cost can be realized.

To achieve the above-mentioned objects, the present invention can be realized as an image processing method having the characteristic units of the above-mentioned image processing device and the ultrasonic diagnostic device as steps and the present invention can be realized as a program including all of these steps. Then, the program not only can be stored in ROM and the like that the image processing device and the ultrasonic diagnostic device include but also can be distributed through a recording medium such as CD-ROM or transmission medium such as a communication network.

Japanese patent application No. 2002-097079 filed on Mar. 29, 2002 is incorporated herein by reference.

BRIEF DESCRIPTION OF THE DRAWINGS

These and other objects, advantages and features of the invention will become apparent from the following description thereof taken in conjunction with the accompanying drawings that illustrate specific embodiments of the invention. In the drawings:

FIG. 4A is a diagram that lines up the acquired tomographic image examples in chronological order.

FIG. 4B is an example of a graph that represents the left ventricular volume (LVV), one of the characteristic values, calculated based on the individual tomographic images in FIG. 3A by a curve (a LVV curve).

FIG. 4C is a diagram that shows the generated synchronization signal based on the calculated LVV curve.

FIG. 5A is an example of an LVV curve.

FIG. 5B is an example of a pseudo R wave that is generated based on the activity of the left ventricle of the heart (the LVV curve) and that corresponds to the R wave in the ECG waveform.

FIG. 6 is a flowchart that shows "the process to generate the pseudo R wave" in the case of generating the pseudo R wave in real time.

FIG. 7A is a diagram that shows an example of the generated synchronization signal.

FIG. 7B shows how the image data to which the synchronization information is added are stored and how only the image data to which the synchronization information is added are read in the ultrasonic diagnostic device according to the first embodiment in schematic form.

FIG. 9A is a diagram that shows the contents of the processing in the image generation unit.

FIG. 9B is a diagram that shows the contents of the processing in the characteristic value extraction unit.

FIG. 9C is a diagram that shows the contents of the processing in the synchronization generation unit and the synchronization information addition unit.

FIG. 9D is a diagram that shows the contents of the processing in the image display unit.

FIG. 18 is a diagram that shows the relationship of mutual acquisition timing in the case of acquiring the image data of the tomographic image and the image data of an image including bloodstream information.

FIG. 19A is an example of the acquired plural tomographic images.

FIG. 19B is an example of the generated synchronization signal waveform.

FIG. 19C is an example of the acquired plural bloodstream images and a diagram that shows how the processing for relating the generated synchronization signal with the bloodstream image is executed.

FIG. 19D is an example of the combined plural images that combine the tomographic images and the bloodstream images.

DESCRIPTION OF THE PREFERRED EMBODIMENT(S)

The embodiments according to the present invention will be explained below with reference to the figures. Note that in the embodiments below, an ultrasonic diagnostic device is taken as an example of the above-mentioned image processing device and will be explained below.

(The First Embodiment)

Figure 1:
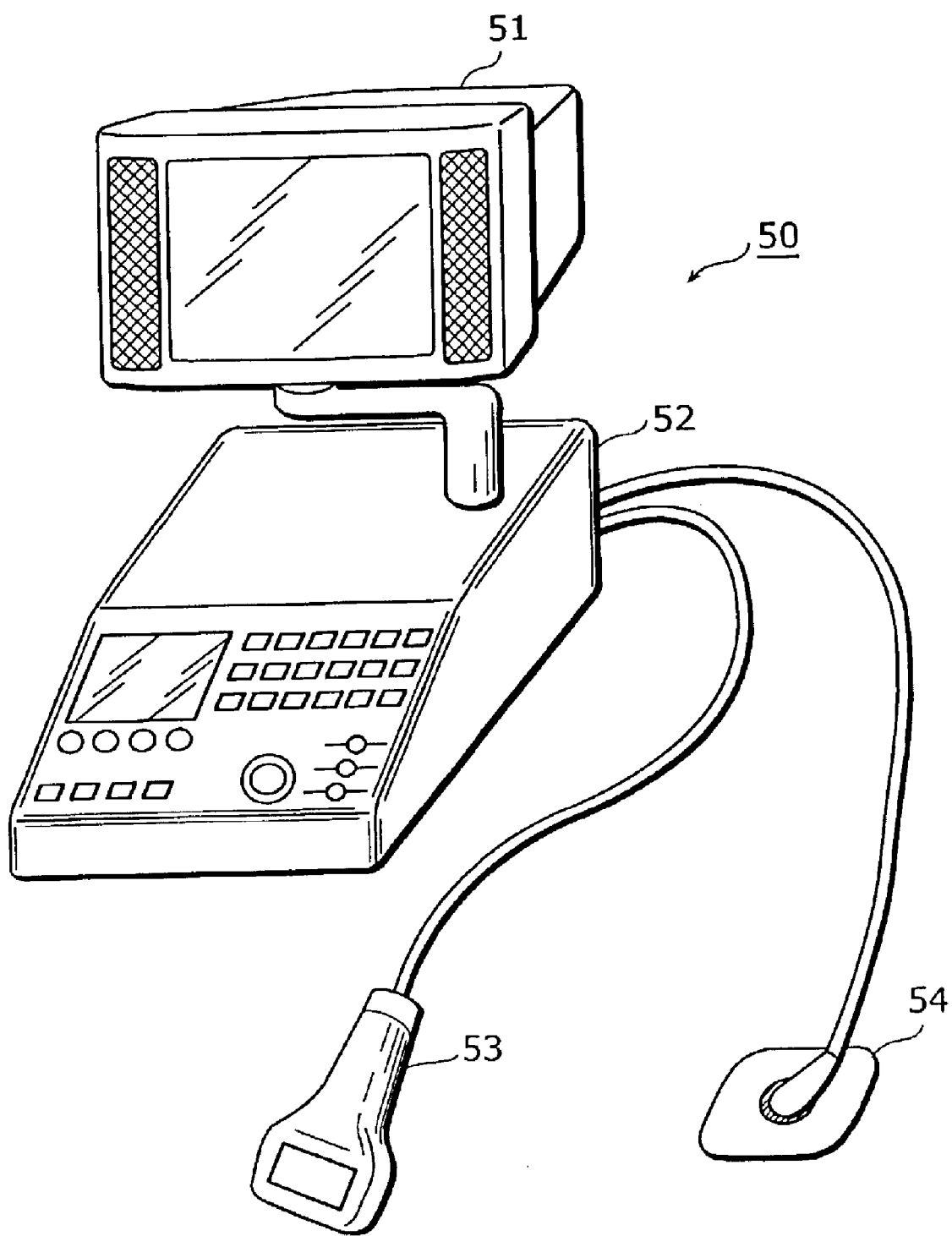
FIG. 1 is an outside view of a conventional ultrasonic diagnostic device.
Figure 2:
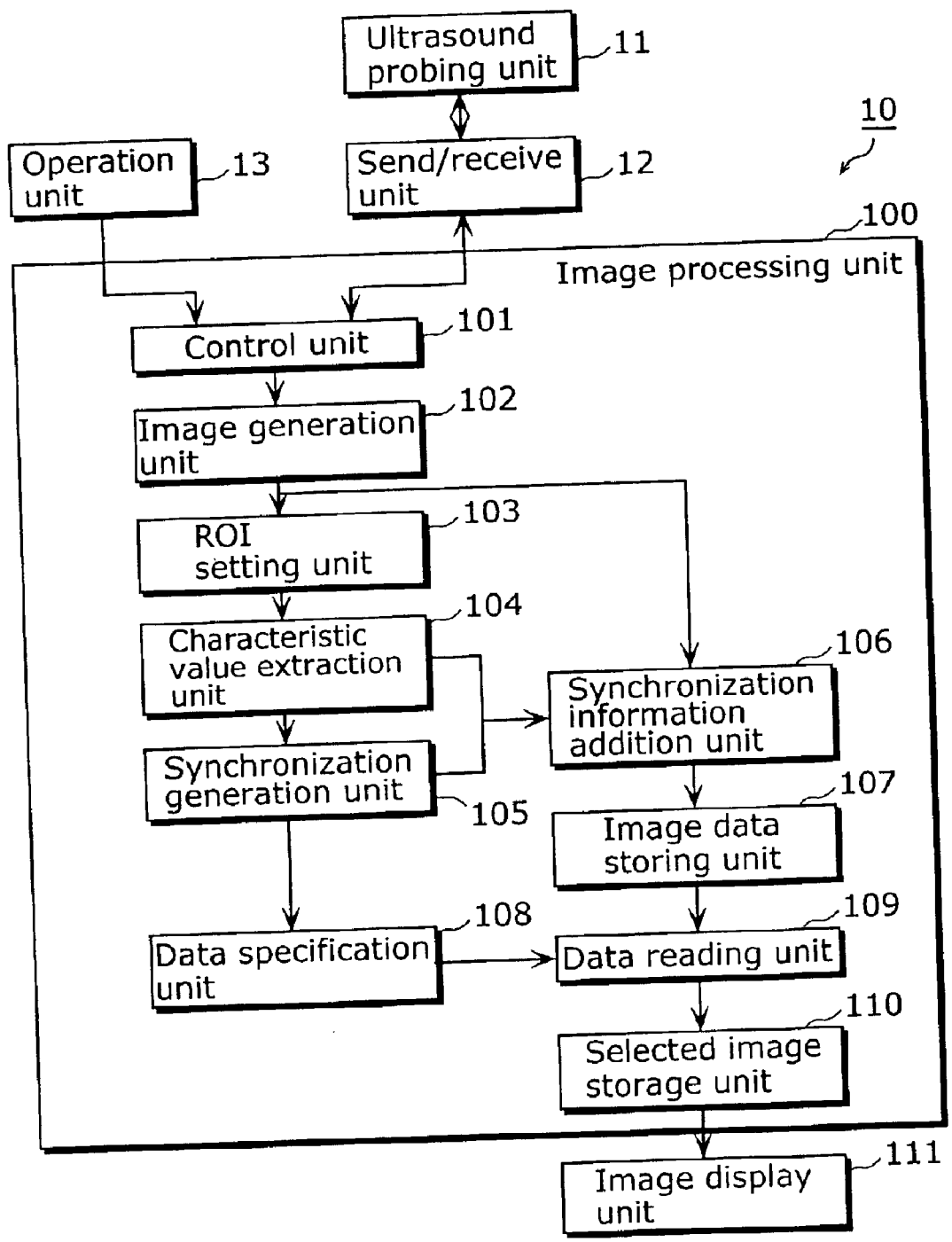
FIG. 2 is a block diagram that shows a functional configuration of an ultrasonic diagnostic device according to the first embodiment.

FIG. 2 is a block diagram that shows a functional configuration of an ultrasonic diagnostic device 10 according to the first embodiment. The present device 10 is an ultrasonic diagnostic device that has a function that generates a synchronization signal from an acquired tomographic image and includes an ultrasonic search unit 11, a send/receive unit 12, an operation unit 13, an image processing unit 100 and an image display unit 111.

The ultrasonic search unit 11 is generally called a probe and is, for example, a probe that performs an electronic scan based on a phased array method. The ultrasonic search unit 11 emits ultrasound (e.g., ultrasonic pulse) based on a control signal received from the send/receive unit 12. Further, the search unit 11 also receives ultrasound (hereafter called "ultrasonic echo") reflected from inside the living body of the test object (hereafter, also called "patient"), converts the ultrasonic echo into an electric signal, and sends the electric signal to the send/receive unit 12.

The send/receive unit 12 is made up of a sender/beam former that has the ultrasonic search unit 11 generate ultrasound and a receiver/beam former that receives an electric signal from the search unit 11 that has detected an ultrasonic echo. The send/receive unit 12 processes the electric signal received from the ultrasonic search unit 11 by amplifying it, and sends the processed electric signal to the image processing unit 100.

The operation unit 13 is equipped with a switch, a touch panel and the like, receives an input from the operator and sends a control signal corresponding to the received input to the image processing unit 100.

Based on the electric signal from the send/receive unit 12, the image processing unit 100 generates Image data of a tomographic image. Further, based on a change of characteristic value (such as a volume and a cross section area of the left ventricle of the heart), the image processing unit 100 generates the synchronization signal. Here, the "image data" refers to data such as two-dimensional brightness data. The image data are generated each time the ultrasonic search unit 11 executes one scan, and are displayed in B mode.

This image processing unit 100 is made up of a control unit 101, an image generation unit 102, an ROI (Region of Interest) setting unit 103, a characteristic value extraction unit 104, a synchronization generation unit 105, a synchronization information addition unit 106, an image data storage unit 107, a data specification unit 108, a data reading unit 109 and a selected image storage unit 110.

The control unit 101 is, for example, a microcomputer equipped with ROM (Read-Only Memory), RAM (Random Access Memory) and the like, and instructs each unit in the image processing unit 100 to execute its own processing, and controls timing of the processing. To be more specific, the control unit 101 controls the send/receive unit 12 that sends an ultrasound and receives an ultrasound echo, and receives and decrypts a control signal and the like sent by the operation unit 13. Further, the control unit 101 sends an electric signal converted from an ultrasound echo that the control unit 101 has received from the send/receive unit 12 to the image generation unit 102.

The image generation unit 102 first receives an electric signal from the send/receive unit 12 through the control unit 101. The image generation unit 102 then executes an amplified calculation, analog-to-digital (A/D) conversion and an interpolation calculation on the received electric signal to generate image data of a tomographic image.

The ROI (Region of Interest) setting unit 103 sets a Region of Interest (ROI) that is a calculation object of the characteristic value to the generated tomographic image and further extracts a contour of the object in this ROI. Generally, plural tomographic images are acquired in chronological order and the ROIs are set for these tomographic images individually.

As for extracting the contour of the object, it is acceptable to accept the contour manually from the operator through the operation unit 13 or to acquire the contour of the ROI by an "automatic contour extraction method" disclosed by Japanese Laid-Open Patent Application No. 2002-224116. This automatic contour extraction method first uses techniques of "digitalization" and "degeneracy" to the tomographic image of the object to extract a rough initial contour and then seeks a fine contour by applying an active contour model (SNAKES) to this initial contour and making a convergence calculation.

Figure 3:
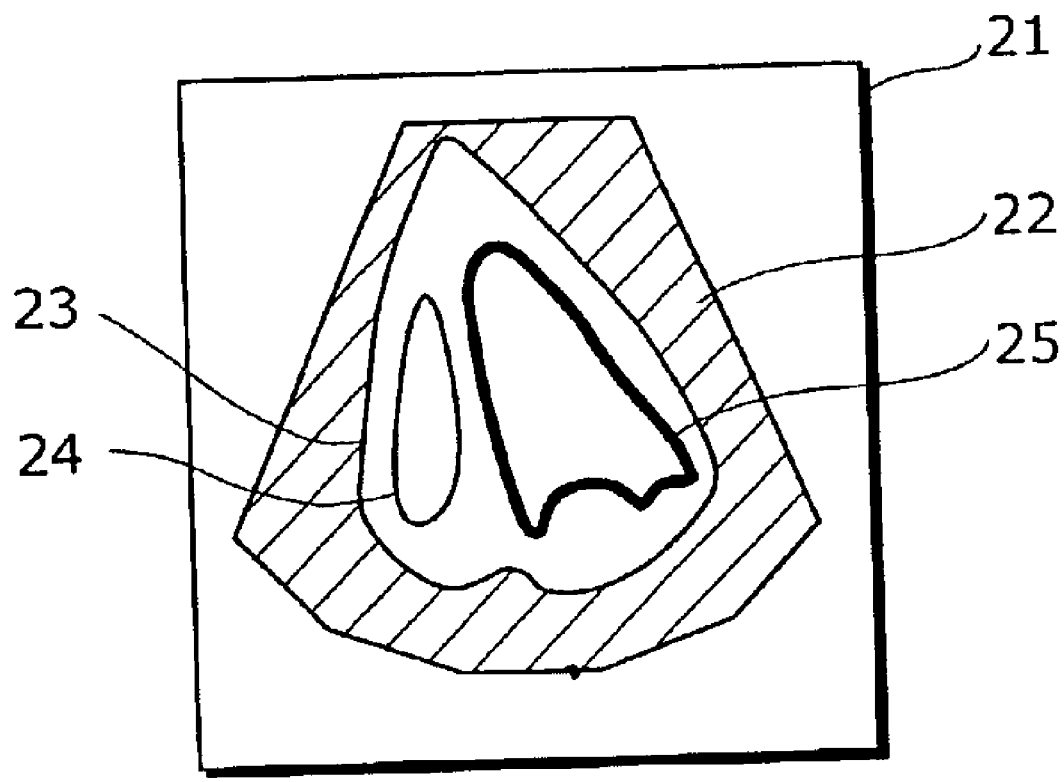
FIG. 3 is a diagram that shows an example of a method for setting an ROI (Region of Intesest) in a tomographic image by the ROI setting unit.

FIG. 3 is a diagram that shows an example of a method for setting an ROI in a tomographic image by the ROI setting unit 103. FIG. 3 shows a tomographic image of a heart which is projected and the left ventricle being set as an ROI. In FIG. 3, an area surrounded by a square 21 is the outer frame of an observational monitor in the image display unit 111 that will be explained later; the fan-shaped part shown by oblique lines inside the outer frame is a whole tomographic image projected by the ultrasonic diagnostic device 10; curves 23 and 24 projected by black thin lines are the contour of the heart; and the inner part surrounded by a black thick curve 25 is the ROI (here, the left ventricle of the heart).

The characteristic value extraction unit 104 extracts or calculates characteristic values (such as a volume and a cross-section of the left ventricle of the heart) of the ROI of the tomographic image specified by the ROI setting unit 103. For example, the radius of the object is calculated from the tomographic image, and the left ventricular volume (LVV) of the heart is calculated by substituting the calculated radius into an approximate expression such as the single plane area length method and the Modified Simpson method.

The synchronization generation unit 105 generates a synchronization signal (e.g. a waveform like an R wave in ECG waveform) based on the extracted characteristic value. For example, there is a method for generating the synchronization signal at the time when the LVV becomes the smallest or a method for generating the synchronization signal that coincides with the change of the LVV (e.g. the R wave of pseudo ECG waveform).

FIG. 4A~FIG. 4C are diagrams that show an example of a method for generating the synchronization signal based on the characteristic value extracted by the characteristic value extraction unit 104. FIG. 4A is a diagram that lines up the acquired tomographic image examples in chronological order. Based on each tomographic image in FIG. 4A, the LVV of the heart V, an example of the characteristic value, is calculated (and represented by ●). FIG. 4B is a graph that represents this by a curve (hereafter called a "left ventricular volume (LVV) curve"). In FIG. 4B, the vertical axis represents the left ventricular volume V and the horizontal axis represents time t. Here, spline interpolation or polynomial expression interpolation (the interpolation curve in this case is represented by (the number of the points −1) degree of polynomial expression) is executed to the calculated LVV of the heart V to generate the LVV curve 33. FIG. 4C is a diagram that shows an example of the generated synchronization signal based on the LVV curve 33. When the extreme value of the LVV curve 33 is detected (in this case, the minimum values 32 and 37), the synchronization pulses 34, 38 (e.g. triangular wave pulse) are generated to coincide with the time when these minimum values are detected. FIG. 4C shows how this is done.

Here, the example using the LVV of the heart as the characteristic value is shown, but it is possible to use, for example, the movement of the beating blood vessel wall without modification or the change in the diameter of the blood vessel as the characteristic value.

In addition, it is acceptable to construct the synchronization generation unit 105 to generate an ECG waveform that is closer to the real ECG waveform artificially. In this case, the synchronization signal that corresponds to the ECG waveform is generated based on the activity of the left ventricle of the heart. The ECG waveform shows a change of active potential of cardiac muscles in action. According to Medical Electronic Measurement (written by Mr. Hiroshi Yagi and published by Sangyo Tosho Publishing Co., Ltd.), the constriction of a heart is produced by electric conduction of nerve or neuroid muscle fiber as a trigger. In other words, the activity of a heart has a close link with the ECG waveform; by monitoring the activity of the heart, it is possible to estimate the ECG waveform and to generate the ECG waveform artificially.

As for a waveform displayed in ECG, there are P wave, Q wave, R wave, S wave, T wave and U wave according to the active phases of the heart, but in the case of measuring the function of the circulatory organs starting from the heart, it is the common practice to use the "R wave". Since the R wave appears when the left ventricle of the heart starts the constriction and its amplitude is large, it is often used as a trigger signal when the function of the heart is diagnosed.

FIG. 5A and FIG. 5B are diagrams that explain a method for generating a synchronization signal corresponding to an ECG waveform artificially. FIG. 5A is an example of the LVV curve. Furthermore, FIG. 5B is an example of a pseudo R wave that is generated based on the activity of the left ventricle of the heart (the LVV curve) and that corresponds to the R wave in the ECG waveform.

Generally, the timing when the R wave appears is about 0.05 seconds before the left ventricle starts the constriction and this is exactly halfway between the time that represents the local minimal value 41 and the local maximal value 42 (the time is T3 and T4, respectively) just before the left ventricle of the heart enters the systole in the LVV curve 33. Consequently, from the LVV curve 33, the minimum value 43 and its time T5 are specified; the local maximal value 42 just before the minimum value 43 and its time T4 are specified; and further the local minimal value 41 just before the local maximal value 42 and its time T3 are specified. FIG. 5B is a concrete example for the shape of the pseudo R wave generated by the synchronization generation unit 105. The R wave in this case has a shape that combines a large isosceles triangle and two small isosceles triangles; as in FIG. 4B, when a~d are defined, "a:b:c:d=10:5:2:1.

There are two methods to generate the pseudo R wave.

One is a method for generating the pseudo R wave in non-real time after the tomographic images are acquired for a predetermined time (e.g. about 10 seconds) in advance. In this case, the ROI is set; the contour is extracted; and the LVV curve 33 is obtained by the extracted contour and the plural tomographic images. The time T3 and T4 are specified from this LVV curve 33 with the above-mentioned procedures and the pseudo R wave is generated in the middle of these two times.

The other is a method for generating the pseudo R wave in real time. In this case, the pseudo R wave is generated by making the predetermined frames (e.g. 10 frames) one set. In this case also, the LVV curve 33 is partially obtained by setting the ROI and extracting the contour. When the minimum value can be specified in the obtained partial LVV curve 33, the times T3 and T4 are specified by going back from the time. Similar to above, the pseudo R wave is generated in the middle of these two times. In the case of 30 [fps], for example, it takes at least 330[ms] to generate a pulse of the pseudo R wave and therefore there is a delay but since there is the time of 33 [ms] between the frames. It is possible to follow the actual activity of the heart.

FIG. 6 is a flowchart that shows "the process to generate the pseudo R wave" in the case of generating the pseudo R wave in real time.

Initially, the image generation unit 102 generates 10 frames of the tomographic image. Based on the generated frames, the characteristic value extraction unit 104 calculates the LVV and memorizes it temporarily (S501). Next, the synchronization generation unit 105 compares each volume value with the standard value (Vs) that is set in advance (S502) and judges whether the minimum value is specified or not (S503). When the synchronization generation unit 105 can specify the minimum value (S503: Yes), it specifies the local maximal value, the local minimal value and each time (T4 and T3) (S504 and S505).

Next, since T4 and T3 are specified, the time of each characteristic point in the pseudo R wave is determined, and therefore, it is possible to generate the pseudo R wave (S507). By the way, when the minimum value cannot be specified (S503: No), the image generation unit 102 generates the next 10 frames of the tomographic image and the same process as above is executed.

The synchronization information addition unit 106 associates the generated characteristic value and synchronization signal information with the timing when the image data is generated and stores the associated image data in the image data storage unit 107.

The image data storage unit 107 is, for example, a memory unit made up of RAM and the like and has a capacity of several dozen to several hundred Mega bytes. The image data storage unit 107 stores the image data associated with and added to the characteristic value (e.g. the volume of the left ventricle of the heart) and the synchronization information by the synchronization information addition unit 106.

By specifying the characteristic value or the synchronization signal information, the data specification unit 108 specifies the information to select the image data that exist in the particular phase in the sequence of image data that changes cyclically or with certain regularity and sends the information to the data reading unit 109.

Based on the information received from the data specification unit 108, the data reading unit 109 reads the applicable image data from the image data storage unit 107 and sends the image data to the selected image storage unit 110.

The selected image storage unit 110 is frame memory or the like for the observational monitor of the image display unit 111 and stores the image data read by the data reading unit 109.

The image display unit 111 reads the image data stored in the selected image storage unit 110 and displays the tomographic image in B mode or the like on a liquid crystal display or the like that is the observational monitor. In addition, the image display unit 111 has a graphic accelerator, DSC (Digital Scan Converter) and the like.

FIG. 7A and FIG. 7B are diagrams that explain a functional overview of the ultrasonic diagnostic device 10 according to the first embodiment. FIG. 7A is a diagram that shows an example of the generated synchronization signal. FIG. 7B shows how the image data to which the synchronization information is added are stored and how only the image data to which the synchronization information is added are read in the ultrasonic diagnostic device 10 in schematic form.

As shown in FIG. 7B, the synchronization information "R" is added to the image data by the synchronization information addition unit 106; the image data are stored in the image data storage unit 107; the data reading unit 109 reads only the image data to which the synchronization information "R" is added from the data storage unit 107.

Here, the synchronization information "R" is added to the tomographic image that causes to generate the synchronization pulse but it is acceptable only if this synchronization information can be uniquely specified. Additionally, it is acceptable to add the image data other than the image data to which the synchronization information "R" is added to other synchronization information such as "P" or "Q" and to add one piece of the image data to plural synchronization information. Further, it is also acceptable to add the characteristic value itself to each image data.

Further, when the synchronization information "R" Is designated by the data specification unit 108, the data reading unit 109 reads only the image data to which the synchronization information "R" (61~65 and the like) is added in sequence from the image data storage unit 107. As for the method for specifying the image data, it is acceptable that the operator designates the synchronization information itself or it is acceptable to designate the image data n frames before or n frames after the image data to which the "R" is added. It is also acceptable to designate plural synchronization information such as the "R" and the "Q", to read the image data to which the synchronization information is added in each cycle and to have the image display unit 111 display them at the same time. As for the timing to update the display, it is acceptable to read automatically from the image data storage unit 107 at an appropriate time interval (e.g. an interval of one second) or to update the display manually when the operation unit 13 has a track ball and a keyboard (not illustrated).

As is described above, since the ultrasonic diagnostic device 10 according to the first embodiment generates the synchronization information from the acquired tomographic image, it is possible to extract the synchronous tomographic image and to diagnose the examined object based on the synchronous tomographic image without inputting the synchronization signal from the outside.

Note that the configuration that generates the pseudo R wave is explained in the first embodiment, but that it is acceptable to generate an ECG waveform other than the R wave such as the P wave and the Q wave. Additionally, in the present embodiment, a practical example in which 10 frames' ultrasound images are acquired and the LLV is calculated based on them is explained, but it is needless to say that the number is not limited to 10.

Further, when the image display device is a CT (Computerized Tomography) device of X-rays, the control unit 101 applies X-rays and controls an X-ray detector. When the image display device is MRI (Magnetic Resonance Imaging), the control unit 101 controls the magnetic field and the pulse column of the measurement area and the detector.

Furthermore, in the first embodiment, the example in which attention is focused on the left ventricle of the heart as the ROI is shown, but the object of the ROI is not limited to the left ventricle of the heart and its shape is also arbitrary. Moreover, the method for setting the ROI is not limited to the above-mentioned method; and it is acceptable to set the ROI by a method other than the above-mentioned method.

(The Second Embodiment)

Figure 8:
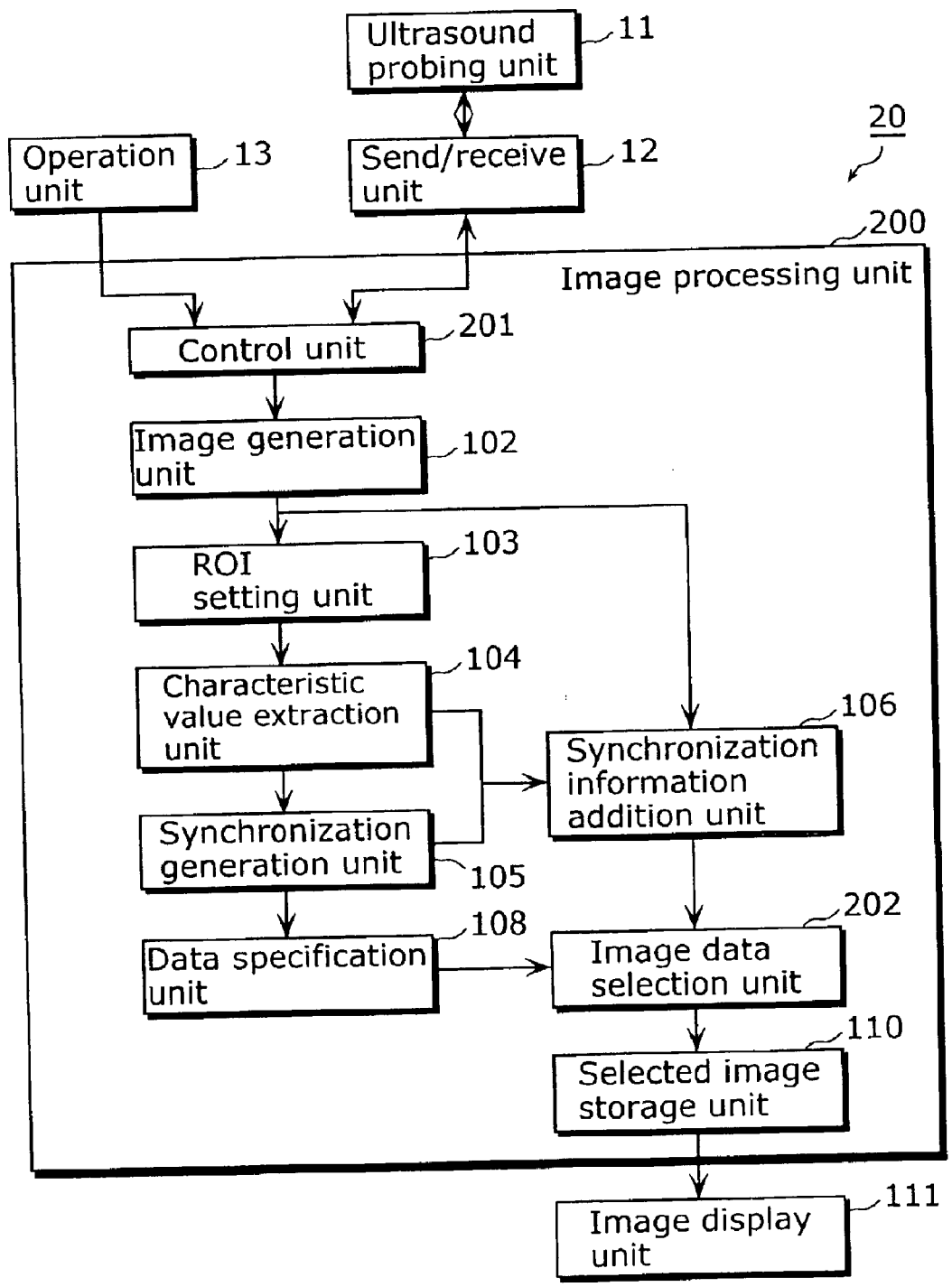
FIG. 8 is a block diagram that shows the functional configuration of an ultrasonic diagnostic device according to the second embodiment.

FIG. 8 is a block diagram that shows the functional configuration of an ultrasonic diagnostic device 20 according to the second embodiment. While the ultrasonic diagnostic device 10 according to the first embodiment stores the tomographic image to which the synchronization information is added temporarily in the image data storage unit 107 and displays the synchronous tomographic image, the present device 20 displays the synchronous tomographic image more rapidly without storing the tomographic image to which the synchronization information is added temporarily. In the following description, the configuration different from the first embodiment is explained in detail, while the common configuration is given the same numbers and the explanation thereof is omitted.

The ultrasonic diagnostic device 20 differs from the ultrasonic diagnostic device 10 in that the device 20 includes an image data selection unit 202 in place of the image data storage unit 107 and the data reading unit 109.

A control unit 201 controls the image data selection unit 202 in place of controlling the image data storage unit 107 and the data reading unit 109 in the first embodiment.

The image data selection unit 202 selects the image data to which the synchronization information is added and that are designated by the data specification unit 108 and discards the image data other than that. The selected image data are sent to the selected image storage unit 110. For this reason, an observer can observe only the tomographic image in the arbitrary phase based on the synchronization signal real time similar to the case of inputting the synchronization signal from the outside.

FIG. 9 is a time chart that shows the flow of processing of each unit in the ultrasonic diagnostic device 20. FIG. 9A is a diagram that shows the contents of the processing in the image generation unit 102; FIG. 9B is a diagram that shows the contents of the processing in the characteristic value extraction unit 104; FIG. 9C is a diagram that shows the contents of the processing in the synchronization generation unit 105 and the synchronization information addition unit 106; and FIG. 9D is a diagram that shows the contents of the processing in the image display unit 111.

As shown in FIG. 9A, initially, the image generation unit 102 generates the image data of the tomographic image based on an electric signal received through the send/receive unit 12 and the control unit 201 (S81).

Next, the characteristic value extraction unit 104 calculates and memorizes the characteristic value (e.g. the LVV of the heart and the like) based on the generated tomographic image (S82). Further, the synchronization generation unit 105 specifies the local maximum value, the local minimal value and the minimum value based on the extracted characteristic value and based on these values, the synchronization information addition unit 106 executes the addition/ non-addition of the synchronization information (e.g. the "R") (-). At this point, to specify the minimum value, it is necessary to compare the value of the LVV for a predetermined period (e.g. one cycle's period).

The image display unit 111 selects only the image data to which the synchronization information is added and updates the display of the tomographic image based on the selected image data (S84). Thereafter, a similar processing is executed to the second frame and the following.

Figures 10A, 10B:
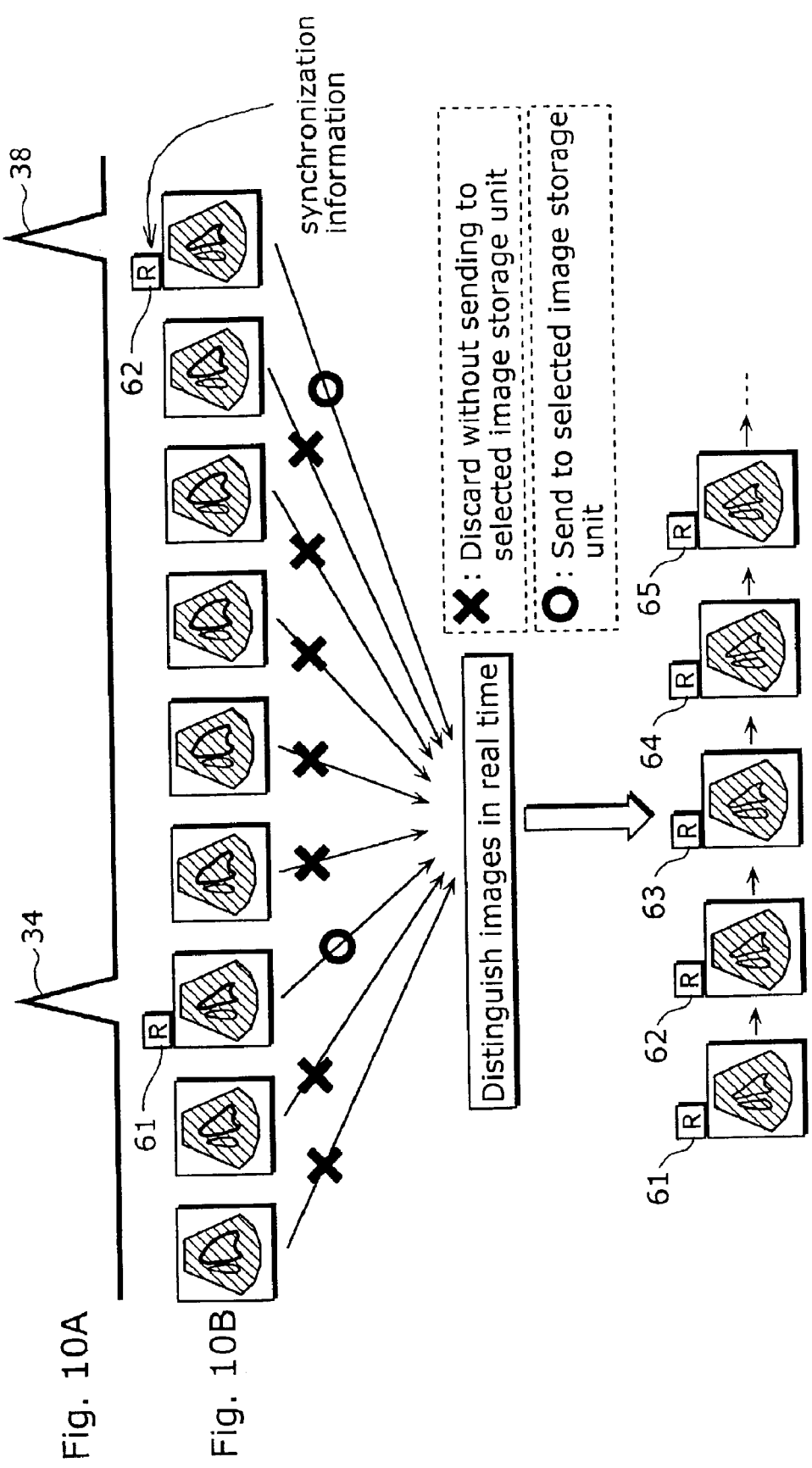
FIG. 10A is a diagram that shows an example of the generated synchronization signal.
FIG. 10B shows how only the image data to which the synchronization information is added are selected in the ultrasonic diagnostic device according to the second embodiment in schematic form.

FIG. 10A and FIG. 10B explain a functional overview of the ultrasonic diagnostic device 20 according to the second embodiment. FIG. 10A is a diagram that shows an example of the generated synchronization signal. FIG. 10B shows how only the image data to which the synchronization information is added are selected and the tomographic images are displayed in the ultrasonic diagnostic device 20 in schematic form.

As shown in FIG. 10B, since the synchronization information "R" is added to the image data by the synchronization information addition unit 106 and the data specification unit 108 instructs the image data selection unit 202 to select only the synchronization information "R", only the image data to which the synchronization information is added (61~65) are selected and become the object of the display.

As is described above, since the ultrasonic diagnostic device 20 according to the second embodiment is configured in order that the synchronization information is added to image data based on the generated synchronization signal and only the synchronous image data can be selected, it is possible to display the synchronous tomographic image without inputting the synchronization signal from the outside, reducing the capacity of memory.

In addition, similar to the first embodiment, it is acceptable to configure in order that the synchronization generation unit 105 generates an ECG waveform artificially.

(The Third Embodiment)

Figure 11:
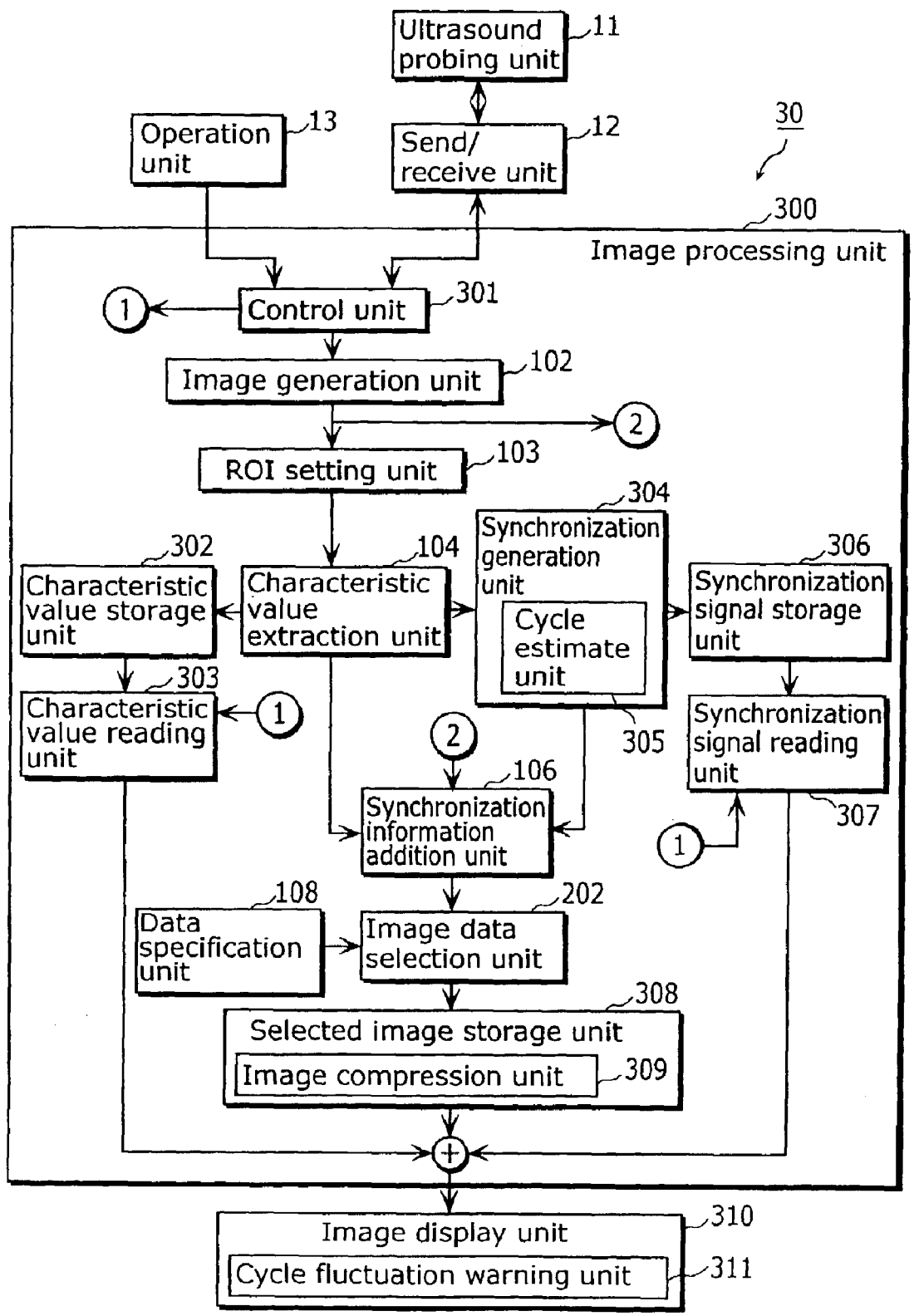
FIG. 11 is a block diagram that shows the functional configuration of an ultrasonic diagnostic device according to the third embodiment.

FIG. 11 is a block diagram that shows the functional configuration of an ultrasonic diagnostic device 30 according to the third embodiment. The present ultrasonic diagnostic device 30 executes a reduced display and a scroll display of the tomographic image and a warning notification when an abnormality about the characteristic value occurs.

Further, the present device 30 displays the extracted characteristic value, the generated synchronization signal and the tomographic image at the same time in one screen.

Note that in the following description, similar to the second embodiment, the configuration different from the first and second embodiments is explained in detail, while the common configuration is given the same numbers and the explanation thereof is omitted.

The ultrasonic diagnostic device 30 differs from the ultrasonic diagnostic device 10 in that the device 30 includes a characteristic value storage unit 302, a characteristic value reading unit 303, a synchronization signal storage unit 306 and the synchronization signal reading unit 307 and has a cycle estimate unit 305 in the synchronization generation unit 304, an image compression unit 309 in the selected image storage unit 308 and a cycle fluctuation warning unit 311 in the image display unit 310.

The control unit 301 has the same function as the control unit 201 of the second embodiment. In addition to this function, the control unit 301 instructs each unit to execute each processing and controls timings of the processing in order to execute the reduced display and the scroll display of the tomographic image and the warning notification when an abnormality about the characteristic value occurs. Additionally, the control unit 301 controls "image display processing" that is described later. Further, the control unit 301 accepts information that represents a reading start point and a reading finish point through the operation unit 13 and sends the information to the characteristic value reading unit 303 and the synchronization signal reading unit 307.

The characteristic value storage unit 302 receives the characteristic value generated by the characteristic value extraction unit 104 and stores the characteristic value in sequence.

Based on the information received from the control unit 301, the characteristic value reading unit 303 reads information of the characteristic value between the reading start point and the reading finish point stored in the characteristic value storage unit 302 and sends the information to the image display unit 310.

The synchronization generation unit 304 is equipped with the cycle estimate unit 305 in addition to the function of the synchronization generation unit 105 of the first embodiment.

The cycle estimate unit 305 estimates the cycle of the synchronization signal by seeking an average value of the cycle of the generated synchronization signal and by executing statistical processing.

The synchronization signal storage unit 306 stores the synchronization signal information generated by the synchronization generation unit 304.

Based on the information received from the control unit 301, the synchronization signal reading unit 307 reads the synchronization signal information between the reading start point and the reading finish point stored in the synchronization signal storage unit 306 and sends the synchronization signal information to the image display unit 310.

The selected image storage unit 308 is equipped with the image compression unit 309 in addition to the same function as the selected image storage unit 110 of the first embodiment. Here, the contents of the frame memory are updated every time the image data are sent from the image data selection unit 202; the new image data are overwritten in sequence; and it is possible to always display the latest tomographic images (in the case of FIG. 12B, 6 pieces).

The image compression unit 309 captures the image data that th e image data selection unit 202 sends to the selection image storage unit 308 temporarily, converts the image data to reduce the display size (e.g. pixel skipping) and stores again plural image data in the frame memory for one screen to display on the observational monitor of the selected image storage unit 110.

Figure 12A:
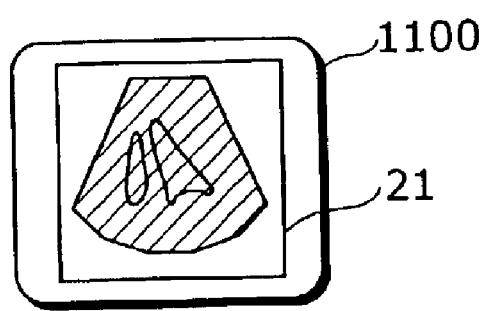
FIG. 12A is a display example of the tomographic image when the image data are not compressed.
Figure 12B:
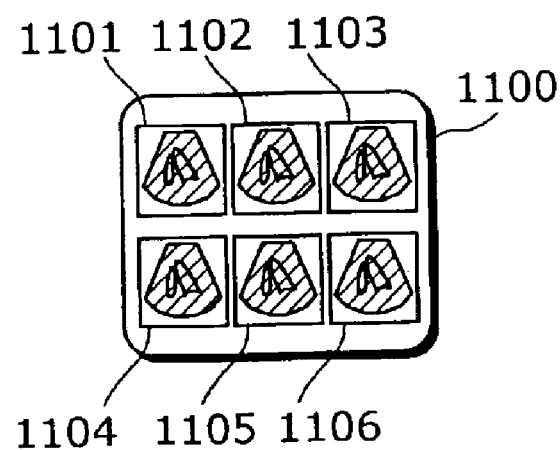
FIG. 12B is a diagram that shows in schematic form a case of displaying six tomographic images at the same time by compressing the image data to one sixth and making the display size smaller.

FIG. 12A and FIG. 12B are diagrams that represent how the image data of the tomographic image are compressed by the image compression unit 309 in schematic form. FIG. 12A is a display example of the tomographic image when the image data are not compressed. FIG. 12B is an example th at displays six tomographic images in one screen by compress ing the image data to one sixth. FIG. 12B is an example of the case to display "n×m (n≧1, m≧1)" pieces of the tomographic images and in this case six pieces (n=3, m=2) of the tomographic images are displayed.

The image compression unit 309 decides the data compression ratio by the screen size that the observational monitor 1100 in the image display unit 310 can display, the data size of the tomographic image and the number of the tomographic images to be displayed (namely m and n). Further, the image compression unit 309 makes it possible to display the plural pieces of the tomographic images that are acquired in succession by performing an interpolative calculation following the generally used sampling technique, seeking the coordinates of the pixels on the tomographic images after the compression and storing the image data in the frame memory that corresponds to the position the operator wants to display.

The image display unit 310 includes the cycle fluctuation warning unit 311 in addition to the function of the image display unit 111 of the first embodiment. Further, the image display unit 310 executes highlight processing and the like to the tomographic image when it displays the latest tomographic image and thus makes it possible to tell easily which is the latest tomographic image.

When an abnormality in the cycle of the synchronization signal generated by the synchronization generation unit occurs, the cycle fluctuation warning unit 311 detects the abnormality by executing statistical processing such as an analysis using regular probability distribution and notifies the abnormality to the operator. As for methods of notification, there is a method for giving a beep as a warning signal and a method for displaying an abnormal area on the screen with a different color.

Figure 13:
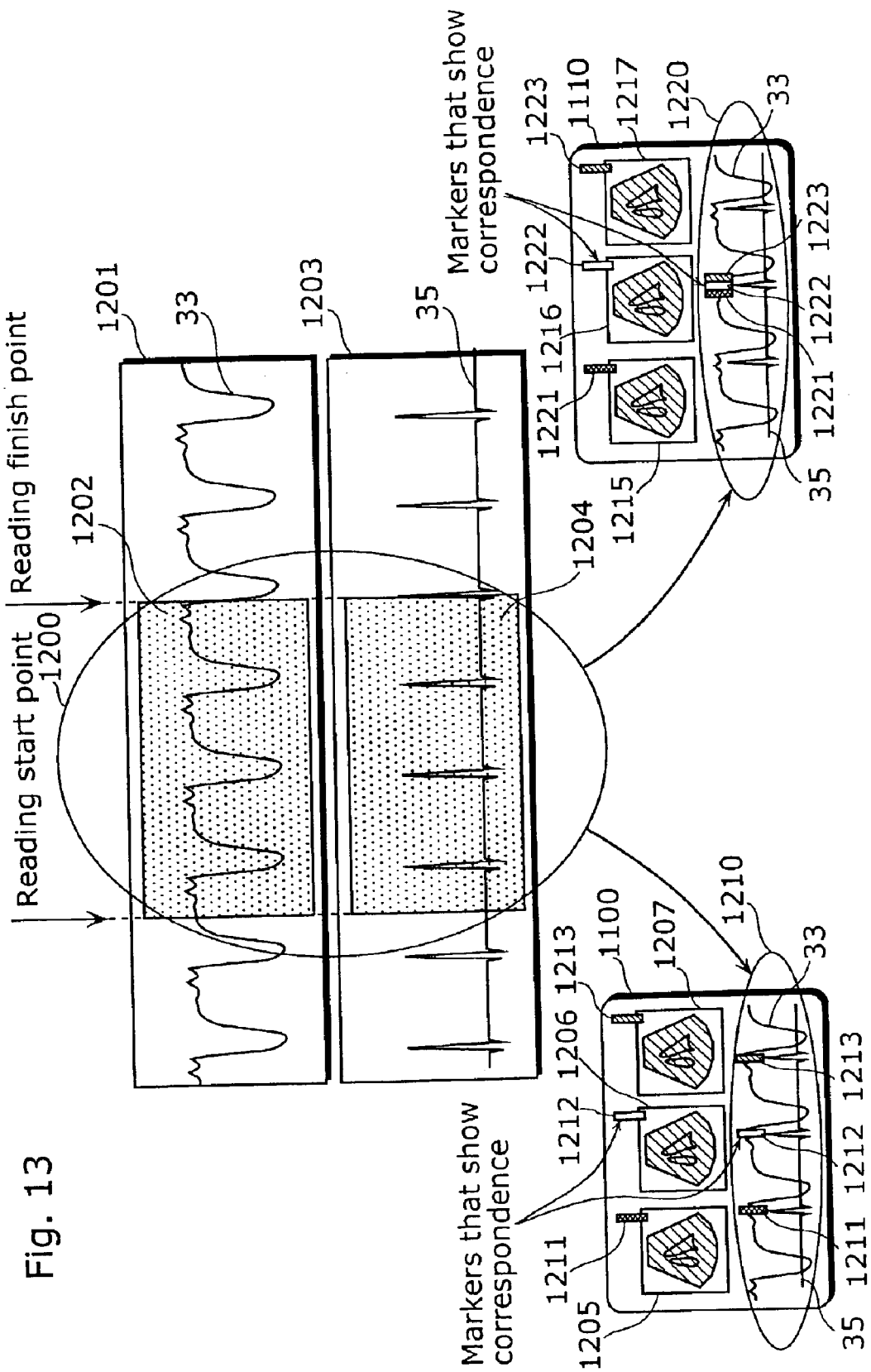
FIG. 13 is an example that shows how the characteristic value and the synchronization signal are displayed by scrolling.

FIG. 13 is an example that shows how the characteristic value and the synchronization signal are displayed by scrolling. In this case, the memory method of data in the characteristic value storage unit 302 and the synchronization signal storage unit 306 is a ring buffer or similar structure. Every time the characteristic value and the synchronization signal are generated coming up with the generation of the image data of the tomographic image, the characteristic value and the synchronization signal are overwritten and stored in sequence. In the case of finishing the storage up to the aftermost storage area, new information is written overwriting old information from the beginning of the storage area.

In the case of displaying the information on the image display unit 310, the information of the characteristic value and the synchronization signal of the image data within the area between "the reading start point" and "the reading finish point" received from the operator is written in the frame memory in the selected image storage unit 308. It is possible to change the positions of the reading start point and the reading finish point, and the characteristic value and the synchronization signal are displayed to be scrolled with time. It is possible to display markers that enable the operator to tell at which timing the displayed characteristic value or the displayed synchronization signal is acquired.

On the observational monitor 1100 in FIG. 13 are displayed three pieces of tomographic images 1205~1207, the characteristic value (the LVV of the heart) curve 33 and the synchronization signal waveform 35 at the same time. Further, on this observational monitor 1100 are indicated the markers 1211~1213 that represent corresponding relationships between each synchronous tomographic image 1205~1207 in a different cycle and the characteristic value curve 33 as well as the synchronization signal waveform 35. On the observational monitor 1101 are indicated the markers 1221~1223 that represent corresponding relationships between each tomographic image 1215~1217 in a different phase in the same cycle and the characteristic value curve 33 as well as the synchronization signal waveform 35. In this case, with the marker 1222 at the center, the three consecutive tomographic images 1215~1217 in a different phase in the same cycle are indicated.

Figure 14A:
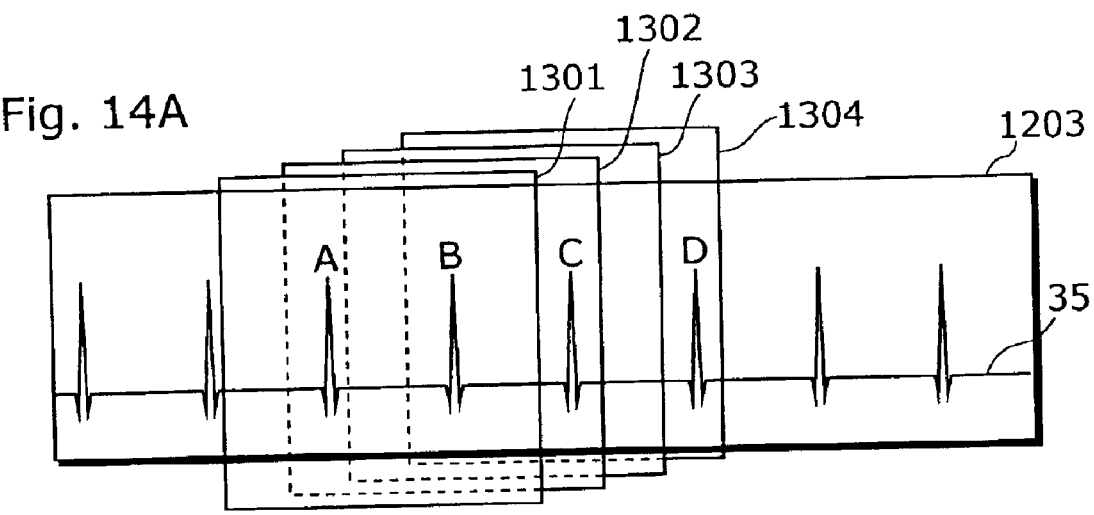
FIG. 14A is a diagram that shows an example of the processing method in the case of changing with time the display object of the synchronization signal and displaying the display object.
Figure 14B:
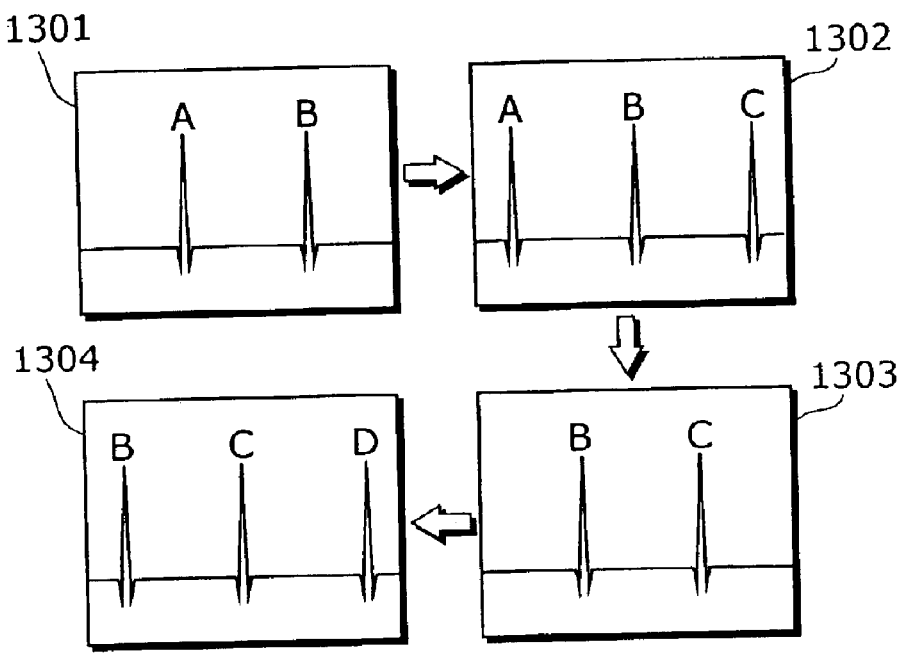
FIG. 14B is a diagram that shows how the actual synchronization signals displayed by the method shown in FIG. 13A change.

FIG. 14A and FIG. 14B shows how the display area of the characteristic value storage unit 302 and the synchronization signal storage unit 306 changes with time. Here, the synchronization signal is explained. The explanation of the characteristic value is exactly alike. FIG. 14A is a diagram that shows an example of the processing method in the case of changing with time the display object of the synchronization signal and displaying the display object. Furthermore, FIG. 14B is a diagram that shows how the actual synchronization signals displayed by the method shown in FIG. 14A change.

FIG. 14A shows how the reading position of the synchronization signal information stored in the synchronization signal storage unit 306 switches with time from Image 1 through Image 4 in numerical order. Coming up with this, the synchronization signals displayed on the observational monitor of the image display unit 310 change as shown in FIG. 14B. The synchronization signals are displayed like a stream from right to left on the screen.

Figure 15:
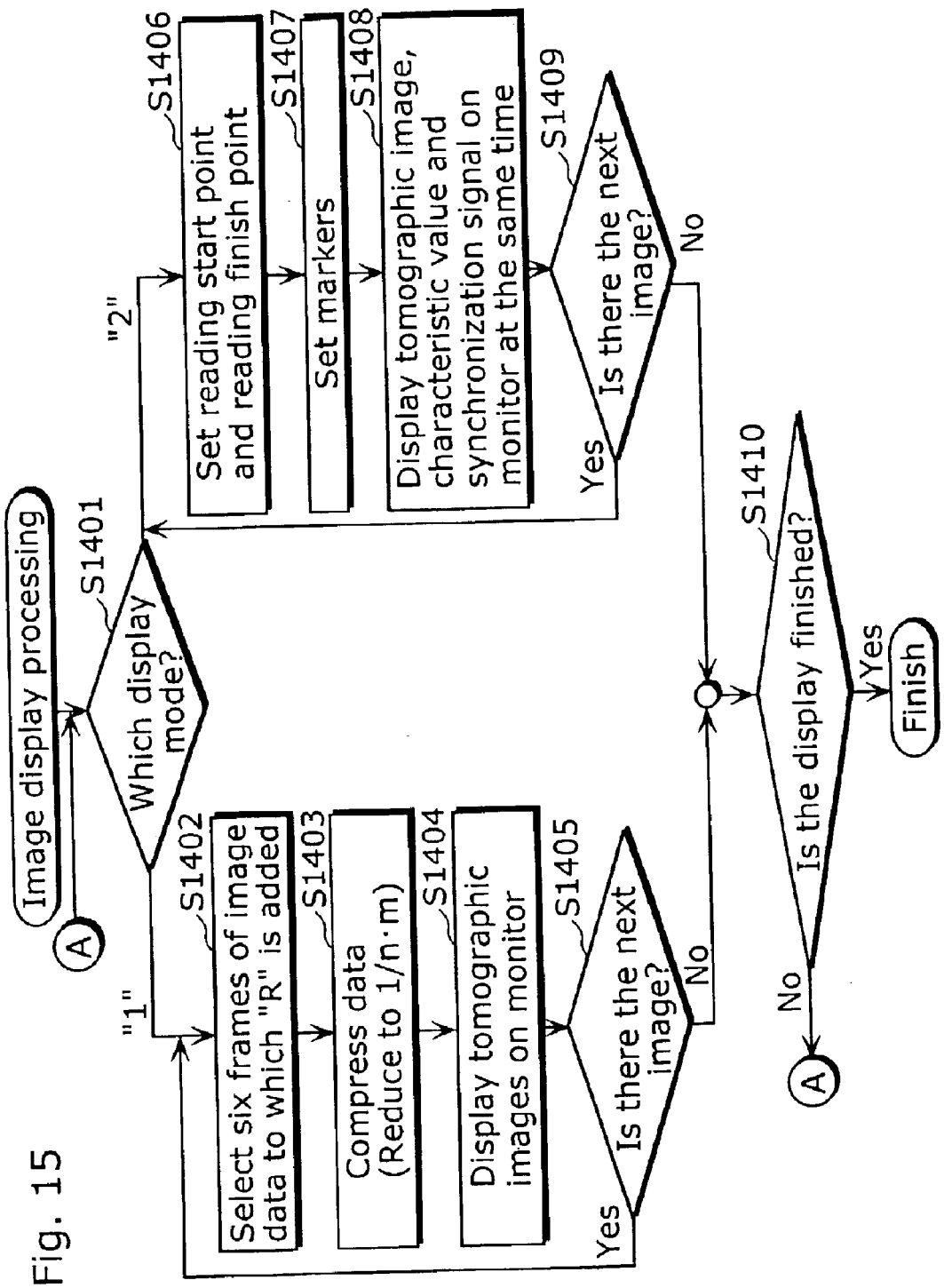
FIG. 15 is a flowchart that shows "image display processing" In the control unit.

FIG. 15 is a flowchart that shows "Image display processing" in the control unit 301 of the ultrasonic diagnostic device 30. In this case, as for the display mode that is the control object, there are "Display mode 1" and "Display mode 2". The Display mode 1 is the mode for displaying the reduced tomographic image as shown in FIG. 12B. On the other hand, as shown in FIG. 13, the Display mode 2 is the mode for displaying (1) the plural synchronous tomographic images in the different cycle, the characteristic value curve and the synchronization signal waveform or (2) the plural tomographic images of the different phase in the same cycle, the characteristic value curve and the synchronization signal waveform.

The control unit 301 receives the type of the display mode from the operator. When the Display mode 1 is selected (S1401), the control unit 301 instructs the data specification unit 108 to display six pieces of the tomographic images to which the synchronization information "R" is added. Next, based on the instruction from the data specification unit 108, the image data selection unit 202 selects six frames (namely, n·m frames: n and m are natural numbers) of image data to which "R" is added and sends them to the selected image storage unit 308 (S1402). In doing this, the image compression unit 309 compresses the received image data to (1/n·m) and stores the compressed image data to the frame memory (S1403). Further, the image display unit 310 displays the tomographic images based on the image data stored in the frame memory on the observational monitor (S1404).

On the other hand, when the Display mode 2 is selected (S14901), based on the reading start point and the reading finish point received from the operator as well as the markers (S1406, S1407), either (1) the plural synchronous tomographic images in the different cycle, the characteristic value curve and the synchronization signal waveform or (2) the plural tomographic images of the different phase in the same cycle, the characteristic value curve and the synchronization signal waveform are displayed (S1408).

Figure 16A:
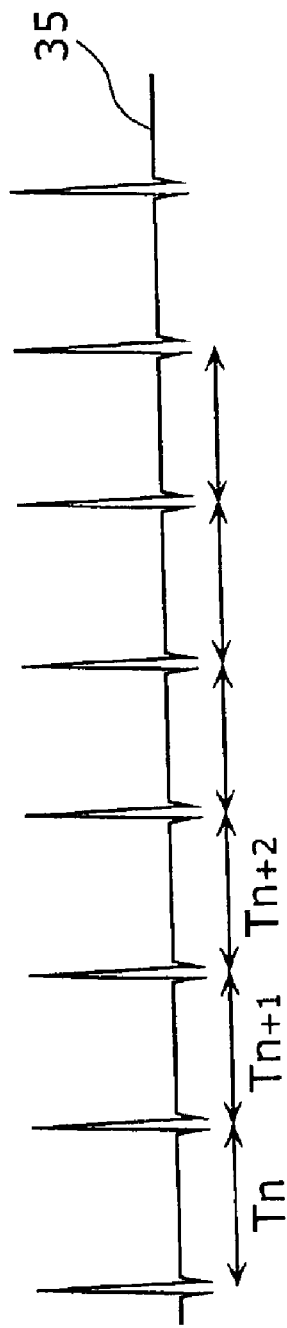
FIG. 16A is a diagram that shows the generated normal synchronization signal waveform.
Figure 16B:
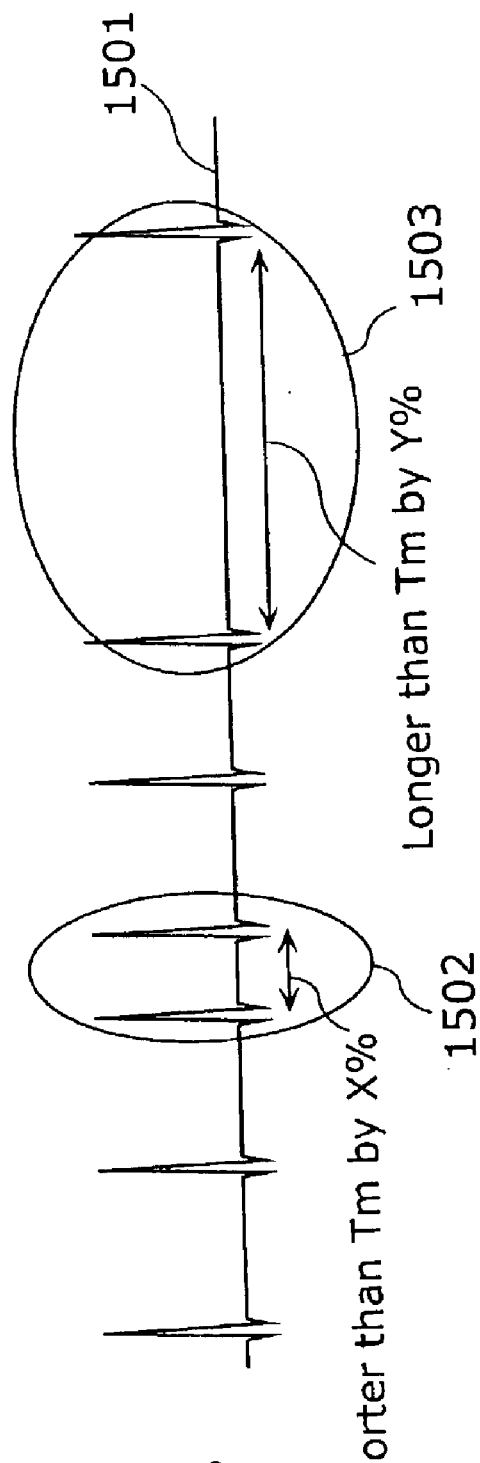
FIG. 16B is a diagram that shows in schematic form how the cycle estimate unit monitors the cycle fluctuation based on the cycle estimated to the generated synchronization signal and issues a warning when the abnormality is observed.

FIG. 16A and FIG. 16B show how the cycle estimate unit 305 monitors the cycle fluctuation based on the cycle estimated to the generated synchronization signal and issues a warning when the abnormality is observed by the cycle fluctuation warning unit 311 in schematic form. FIG. 16A is a diagram that shows the generated normal synchronization signal waveform 35. FIG. 16B is a diagram that shows in schematic form how the cycle estimate unit 305 monitors the cycle fluctuation based on the cycle estimated to the generated synchronization signal and issues the warning when the abnormality is observed.

In general, in the case of generating a synchronization signal focusing attention on the same characteristic value and observing a living body, the synchronization signals will be generated in an almost regular cycle. But when the cycle of the generated synchronization signals fluctuates suddenly, the probability that an abnormality of some kind occurs is great and it is necessary to notify the observer. In the case of FIG. 16B, the cycle fluctuation warning unit 311 calculates the average value Tm of the generated synchronization signals. When the synchronization signal becomes shorter than this Tm by X % or longer than this Tm by X %, the cycle fluctuation warning unit 311 notifies the observer by a warning sound, changing the color of the display, or the like.

In FIG. 11, the ultrasonic diagnostic device 30 is configured to comprise the cycle fluctuation warning unit 311 and to execute a warning notification when the cycle of the synchronization signals fluctuates. It is acceptable that the ultrasonic diagnostic device 30 is configured to comprise a characteristic value fluctuation warning unit and to execute a warning notification when the characteristic value fluctuates abnormally. In this case, the object whose fluctuation is detected is not the cycle. The maximum value, the minimum value and the difference between the maximum value and the minimum value of the LVV of the heart described above are the objects. Using the average value of these values or the like, the characteristic value fluctuation warning unit monitors the ever-changing characteristic value and notifies an observer by sounding a warning or the like when an abnormal value is detected.

As is described, the ultrasonic diagnostic device 30 according to the third embodiment makes it possible to execute the reduced display, the scroll display of the tomographic image and the warning notification when an abnormality in the characteristic value occurs.

Note that it is acceptable to configure the ultrasonic diagnostic device 30 to generate the ECG waveform artificially in the synchronization generation unit 304 similar to the first embodiment.

(The Fourth Embodiment)

Figure 17:
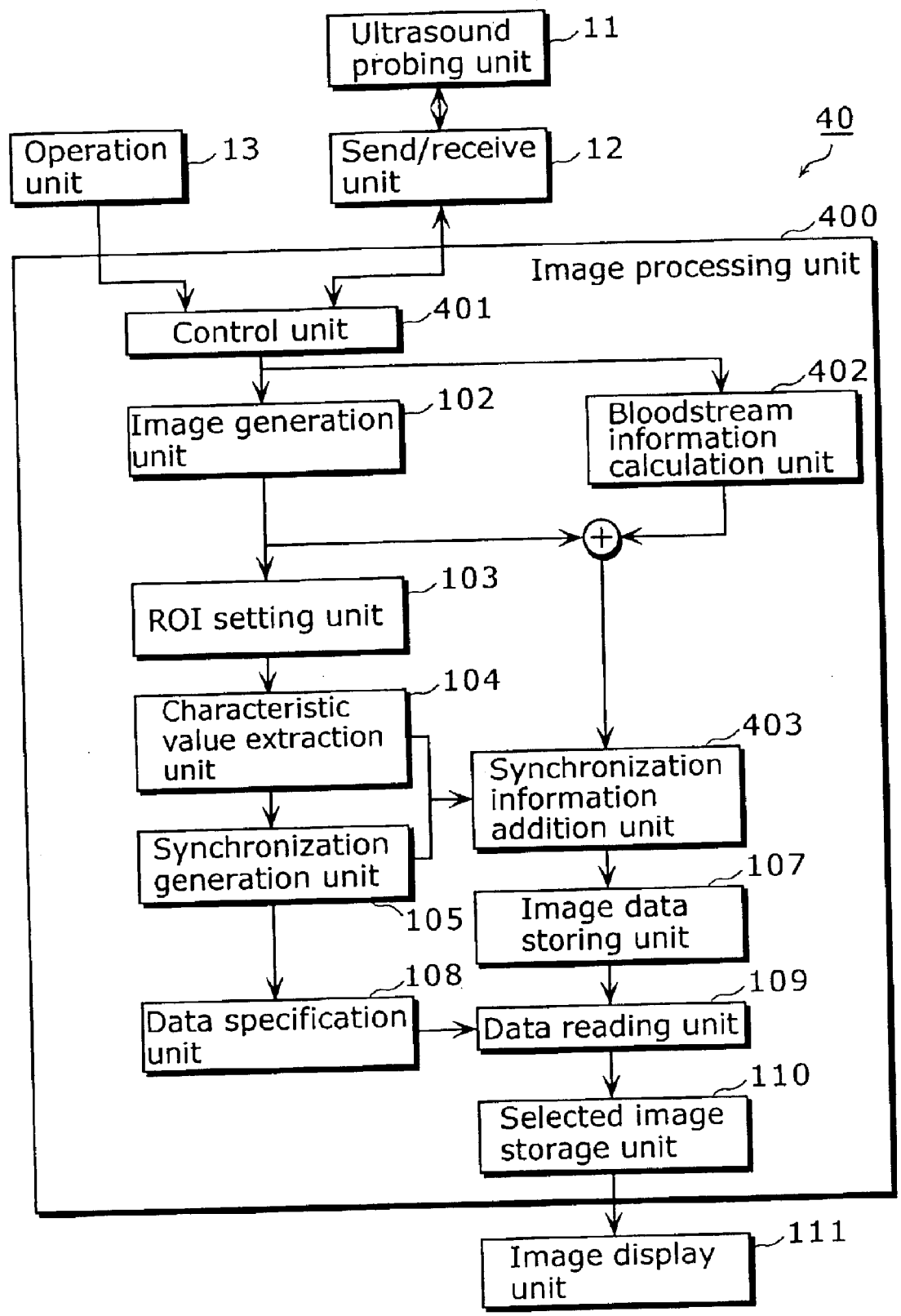
FIG. 17 is a block diagram that shows the functional configuration of an ultrasonic diagnostic device according to the fourth embodiment.

FIG. 17 is a block diagram that shows the functional configuration of an ultrasonic diagnostic device 40 according to the fourth embodiment.

In the following description, the configuration different from the first embodiment is explained in detail, while the common configuration is given the same numbers and the explanation thereof is omitted.

The ultrasonic diagnostic device 40 differs from the ultrasonic diagnostic device 10 in that the device 40 includes a bloodstream information calculation unit 402 that generates an image including the bloodstream information. Here, "the image including the bloodstream information (hereafter called the bloodstream image)" is the image that is generally called the color Doppler. "The color Doppler" is a bloodstream image that uses the Doppler effect of the ultrasound by a moving reflection (a group of red blood cells in the case of bloodstream), overlaps two-dimensional distribution such as bloodstream information of a heart or a blood vessel on the tomographic image of the tissue, and displays the overlapped image in colors in real time. Using this color Doppler, it is possible to grasp the bloodstream information in the body part visually by representing the components of velocity that are coming to and going away from the ultrasound probing unit 11 with the images of different colors, overlapping the components of velocity on the tomographic images of the tissue, and displaying the overlapped images.

The control unit 401 has the function of the control unit 101 of the first embodiment and controls the send/receive unit 12 to send/receive the ultrasound to acquire the tomographic image and the ultrasound to acquire the bloodstream information based on a rule set in advance (e.g. to acquire alternatively) to acquire the image data of the bloodstream image while acquiring the image data of the tomographic image. Further, the control unit 401 sends the two kinds of electric signals received from the send/receive unit 12 separately to the image generation unit 102 and the bloodstream information calculation unit 402 following the above-mentioned rule.

The bloodstream information calculation unit 402 generates the bloodstream information that shows physical characteristics (such as bloodstream velocity, velocity dispersion and the direction of bloodstream) collected by the sampling rate regulated in advance and generates the image data of the bloodstream image based on this bloodstream information.

The synchronization information addition unit 403 adds the image data of the tomographic image to the image data of the bloodstream image as one set of data, adds the same synchronization information to the added image data and stores the added image data in the image data storage unit 107.

FIG. 18 is a diagram that shows the relationship of mutual acquisition timing in the case of acquiring the image data of the tomographic image and the image data of the bloodstream image. Generally, in the case of acquiring the color Doppler image, as shown in FIG. 18, while acquiring the image data of the tomographic image, the control unit 401 collects data for bloodstream information during the interim. Consequently, when the color Doppler image is displayed by the ultrasonic diagnostic device, the frame rate drops (generally, about 10 [fps]). In the case of displaying the color Doppler image, the synchronization information addition unit 403 overlaps the tomographic image 1701 of gray scale on the bloodstream image 1702 that represents the bloodstream speed with warm color/cold color and generates the combined image 1703. In addition, as shown in FIG. 18, the synchronization information addition unit 403 associates the tomographic image 1701 with the bloodstream image 1702 acquired immediately after as one set of data, adds the same synchronization information to the associated image and stores the associated image in the image data storage unit 107.

FIG. 19A~FIG. 19C are diagrams that show how the processing to relate the bloodstream image to the generated synchronization signal is executed. FIG. 19A is an example of the acquired plural tomographic images. FIG. 19B is an example of the generated synchronization signal waveform. FIG. 19C is an example of the acquired plural bloodstream images and a diagram that shows how the processing for relating the generated synchronization signal with the bloodstream image is executed. FIG. 19D is an example of the combined plural images that combine the tomographic images and the bloodstream images. As shown in FIG. 19A~FIG. 19C, the synchronization information addition unit 403 associates the synchronization signal 1802 generated based on the tomographic image 1801 with the bloodstream image 1803 as one set of data, adds the same synchronization information "R" to the associated image and stores the associated image in the image data storage unit 107. Further, the synchronization information addition unit 403 generates the color Doppler image 1804 by combining the tomographic image 1801 and the bloodstream image 1803 that are associated.

As is described above, since the ultrasonic diagnostic device 40 according to the fourth embodiment generates the synchronization signal from the acquired tomographic image and displays a color Doppler image of bloodstream and the like based on this synchronization signal, it is possible to associate an ordinary tomographic image with the color Doppler image that have a temporally constant relationship without inputting the synchronization signal from the outside.

In addition, similar to the first embodiment, it is acceptable to configure the ultrasonic diagnostic device 40 in order to generate the ECG waveform artificially in the synchronization generation unit 105.

What is claimed is:

1. An image processing device that processes a tomographic image of an object that acts cyclically, the image processing device comprising:

an image acquisition unit operable to acquire a sequence of image data of the tomographic image of the object by sampling at a constant rate during a predetermined time that is one cycle or more;

a volume value calculation unit operable to extract contours of the object that change with a passage of time by using the acquired sequence of image data and to calculate volume values of the object based on the extracted contours; and a synchronization signal generation unit operable to generate a synchronization signal that indicates a timing of same phase in the action of the object based on temporal changes of the calculated volume values.

2. The image processing device according to claim 1 further comprising:

a synchronization information addition unit operable to discriminate a phase timing by which individual image data is sampled in the sequence of image data based on the generated synchronization signal and to add synchronization information that indicates that phase timings are the same in plural image data.

3. The image processing device according to claim 2, wherein the image acquisition unit is operable to generate bloodstream information which represents physical characteristics of a bloodstream by sampling based on predetermined rules, and the image processing device further comprises:

a bloodstream image generation unit operable to generate image data of a bloodstream image based on the generated bloodstream information; and a correspondence unit operable to associate image data of the tomographic image to which the synchronization information is added with image data of the bloodstream image based on the synchronization signal.

4. The image processing device according to claim 3, wherein the correspondence unit associates image data of a bloodstream image based on sampled data immediately after the image data of the tomographic image are sampled with the image data of the tomographic image.

5. The image processing device according to claim 2 further comprising:

an image storage unit operable to store the sequence of image data including the image data to which the synchronization information is added.

6. The image processing device according to claim 5 further comprising:

an image read-out unit operable to read out image data to which the synchronization information is added from the image storage unit; and a display unit operable to display a tomographic image based on the read-out image data.

7. The image processing device according to claim 6, wherein the synchronization signal generation unit specifies a minimum volume value among the calculated volume values and generates the synchronization signal based on the timing by which the image data that corresponds to the specified minimum value is sampled.

8. The image processing device according to claim 7, wherein the synchronization signal is a synchronization signal including a pulse waveform and indicates the timing of same phase by a timing of a peak of the pulse waveform.

9. The image processing device according to claim 8 further comprising:

volume value storage unit that stores information which represents the calculated volume values; and a synchronization signal storage unit that stores information that represents the generated synchronization signal, wherein the display unit reads out information that represents the volume values and information that represents the synchronization signal, and wherein the display unit displays the information that represents the volume values and information that represents the synchronization signal together with the tomographic image.

10. The image processing device according to claim 9, further comprising a reception unit operable to receive settings of a reading start point and a reading finish point, wherein the display unit further reads out information that represents volume values between the set reading start point and the set reading finish point and information that represents the synchronization signal, and wherein the display unit displays the information that represents volume values between the set reading start point and the set reading finish point and information that represents the synchronization signal together with the tomographic image.

11. The image processing device according to claim 10, further comprising a marker reception unit operable to receive settings of markers, wherein the display unit further displays the set markers such that the volume value, the synchronization signal and the tomographic image indicate the same phase.

12. The image processing device according to claim 8, wherein the display unit includes:

a data compression unit that compresses the read-out image data;

a memory storage unit that stores the compressed image data into frame memory; and an image display unit that reads out data from the frame memory and displays the tomographic image.

13. The image processing device according to claim 12, wherein the image display unit reads out a plurality of data from the frame memory and displays plural tomographic images.

14. The image processing device according to claim 13, wherein the image display unit displays the plural tomographic images by updating in sequence a temporally old part of the data among the plurality of data from the frame memory.

15. The image processing device according to claim 6, wherein the synchronization signal generation unit includes:

a minimum value specification unit that specifies a minimum volume value among the calculated volume values;

a local maximal value specification unit that specifies a local maximal volume value immediately before the specified minimum volume value; and a local minimal value specification unit that specifies a local minimal volume value immediately before the specified local maximal volume value, and the synchronization signal generation unit generates the synchronization signal at a halfway timing between a timing when the image data that correspond to the specified local maximal volume value is sampled and a timing when the image data that correspond to the specified local minimal volume value is sampled.

16. The image processing device according to claim 15, wherein the synchronization signal is an R wave of an artificial electrocardiogram signal and indicates the timing of same phase by a timing of a peak of the R wave.

17. The image processing device according to claim 15, wherein the synchronization signal is a synchronization signal including a pulse waveform and indicates the timing of same phase by a timing of a peak of the pulse waveform.

18. The image processing device according to claim 1 further comprising:

a cycle estimate unit operable to judge whether a cycle of the generated synchronization signal is within a certain standard value or not; and a warning notification unit operable to issue a predetermined warning if the cycle is judged to not be within the certain standard value.

19. An ultrasonic diagnostic device that generates and displays a tomographic image of an object that acts cyclically, the ultrasonic diagnostic device comprising:

an image acquisition unit operable to acquire a sequence of image data of the tomographic image of the object by sampling at a constant rate during a predetermined time that is one cycle or more;

a volume value calculation unit operable to extract contours of the object that change with a passage of time by using the acquired sequence of image data and to calculate volume values of the object based on the extracted contours, a synchronization signal generation unit operable to generate a synchronization signal that indicates a timing of the same phase in the action of the object based on temporal changes of the calculated volume values;

a synchronization information addition unit operable to discriminate a phase timing by which individual image data is sampled in the sequence of image data based on the generated synchronization signal and to add synchronization information that indicates that phase timings are the same in plural image data; and a display unit operable to display a tomographic image based on the synchronous image data to which the synchronization information is added.

20. An image processing method for processing a tomographic image of an object that acts cyclically, the method comprising:

acquiring a sequence of image data of the tomographic image of the object by sampling at a constant rate during a predetermined time that is one cycle or more;

extracting contours of the object that change with a passage of time using the acquired sequence of image data and calculating volume values of the object based on the extracted contours; and generating a synchronization signal that indicates a timing of same phase in the action of the object based on temporal changes of the calculated volume values.

21. The image processing method according to claim 20 further comprising:

discriminating a phase timing by which individual image data is sampled in the sequence of image data based on the generated synchronization signal and adding synchronization information that indicates that phase timings are the same in plural image data.

22. The image processing method according to claim 21, wherein said acquiring comprises generating bloodstream information which represents physical characteristics of a bloodstream by sampling based on predetermined rules, and the image processing method further comprises:

generating image data of a bloodstream image based on the generated bloodstream information; and associating image data of the tomographic image to which the synchronization information is added with image data of the bloodstream image based on the synchronization signal.

23. A program for an image processing device that processes a tomographic image of an object that acts cyclically, the program causing a computer to execute a method comprising:

acquiring a sequence of image data of the tomographic image of the object by sampling at a constant rate during a predetermined time that is one cycle or more;

extracting contours of the object and calculating volume values of the object based on the extracted contours that change with a passage of time using the acquired sequence of image data; and generating a synchronization signal that indicates a timing of same phase in the action of the object based on temporal changes of the calculated volume values.

24. The program according to claim 23 further causing the computer to execute a method comprising:

discriminating a phase timing by which individual image data is sampled in the sequence of image data based on the generated synchronization signal and adding synchronization information that indicates that phase timings are the same in plural image data.

25. The program according to claim 24, wherein said acquiring comprises generating bloodstream information which represents physical characteristics of a bloodstream by sampling based on predetermined rules, and the program further causes the computer to execute a method comprising:

generating image data of a bloodstream image based on the generated bloodstream information; and associating image data of the tomographic image to which the synchronization information is added with the image data of the bloodstream image.

26. A program for an ultrasonic diagnostic device that generates and displays a tomographic image of an object that acts cyclically, the program causing a computer to execute a method comprising:

acquiring a sequence of image data of the tomographic image of the object by sampling at a constant rate during a predetermined time that is one cycle or more;

extracting contours of the object and calculating volume values of the object based on the extracted contours that change with a passage of time using the acquired sequence of image data, generating a synchronization signal that indicates a timing of same phase in the action of the object based on temporal changes of the calculated volume values;

discriminating a phase timing by which individual image data is sampled in the sequence of image data based on the generated synchronization signal and adding synchronization information that indicates that phase timings are the same in plural image data; and displaying the tomographic image based on synchronous image data to which the synchronization information is added.

27. A recording medium that a computer can read and in which a program for an image processing device that processes a tomographic image of an object that acts cyclically is recorded, wherein the program causes a computer to execute a method comprising:

acquiring a sequence of image data of the tomographic image of the object by sampling at a constant rate during a predetermined time that is one cycle or more;

extracting contours of the object and calculating volume values of the object based on the extracted contours that change with a passage of time using the acquired sequence of image data; and generating a synchronization signal that indicates a timing of same phase in the action of the object based on temporal changes of the calculated volume values.

28. A recording medium that a computer can read and in which a program for an ultrasonic diagnostic device that generates and displays a tomographic image of an object that acts cyclically is recorded, wherein the program causes the computer to execute a method comprising:

acquiring a sequence of image data of the tomographic image of the object by sampling at a constant rate during a predetermined time that is one cycle or more;

extracting contours of the object and calculating volume values of the object based on the extracted contours that change with a passage of time using the acquired sequence of image data:

generating a synchronization signal that indicates a timing of same phase in the action of the object based on temporal changes of the calculated volume values;

discriminating a phase timing by which individual image data is sampled in the sequence of image data based on the generated synchronization signal and for adding synchronization information that indicates that phase timings are the same in plural image data; and display the tomographic image based on synchronous image data to which the synchronization information is added.

* * * * *